US008044230B2

(12) United States Patent
Glinka

(10) Patent No.: US 8,044,230 B2
(45) Date of Patent: Oct. 25, 2011

(54) WATER-SOLUBLE PRODRUGS OF CHLORAMPHENICOL, THIAMPHENICOL, AND ANALOGS THEREOF

(75) Inventor: Tomasz W. Glinka, Cupertino, CA (US)

(73) Assignee: Intervet Inc., Summit, NJ (US)

( * ) Notice: Subject to any disclaimer, the term of this patent is extended or adjusted under 35 U.S.C. 154(b) by 858 days.

(21) Appl. No.: 11/953,972

(22) Filed: Dec. 11, 2007

(65) Prior Publication Data

US 2008/0146640 A1 Jun. 19, 2008

Related U.S. Application Data

(60) Provisional application No. 60/874,860, filed on Dec. 13, 2006.

(51) Int. Cl.
C07C 229/00 (2006.01)
C07D 211/78 (2006.01)
C07D 285/14 (2006.01)
C07D 413/00 (2006.01)
A61K 31/44 (2006.01)
A61K 31/41 (2006.01)
A61K 31/225 (2006.01)

(52) U.S. Cl. ........ 560/155; 546/286; 548/136; 548/241; 514/344; 514/363; 514/548

(58) Field of Classification Search .................. None
See application file for complete search history.

(56) References Cited

U.S. PATENT DOCUMENTS

| 2,671,748 | A | 3/1954 | Crooks |
| 3,405,165 | A | 10/1968 | Rebstock |
| 3,475,470 | A | 10/1969 | Rebstock |
| 3,740,411 | A | 6/1973 | Akiyama et al. |
| 3,770,889 | A | 11/1973 | Gutschick et al. |
| 3,950,360 | A | 4/1976 | Aoki et al. |
| 3,984,564 | A | 10/1976 | Aoki et al. |
| 4,199,569 | A | 4/1980 | Chabala et al. |
| 4,310,519 | A | 1/1982 | Albers-Schonberg et al. |
| 4,311,857 | A | 1/1982 | Nagabhushan |
| 4,582,918 | A | 4/1986 | Nagabhushan et al. |
| 4,743,700 | A | 5/1988 | Jommi et al. |
| 4,820,695 | A | 4/1989 | Debono et al. |
| 4,876,352 | A | 10/1989 | Schumacher et al. |
| 4,916,154 | A | 4/1990 | Asato et al. |
| 4,973,750 | A | 11/1990 | Nagabhushan et al. |
| 5,082,863 | A | 1/1992 | Apelian et al. |
| 5,089,480 | A | 2/1992 | Gibson et al. |
| 5,105,009 | A | 4/1992 | Jommi et al. |
| 5,227,494 | A | 7/1993 | Schumacher et al. |
| 5,288,710 | A | 2/1994 | Cvetovich |
| 5,352,832 | A | 10/1994 | Wu et al. |
| 5,382,673 | A | 1/1995 | Clark et al. |
| 5,399,717 | A | 3/1995 | Cvetovich et al. |
| 5,567,844 | A | 10/1996 | Jommi et al. |
| 5,663,361 | A | 9/1997 | Towson et al. |
| 5,958,888 | A | 9/1999 | Macy et al. |
| 5,965,603 | A | 10/1999 | Johnson et al. |
| 6,054,434 | A | 4/2000 | Kropp et al. |
| 6,136,838 | A | 10/2000 | Chern et al. |
| 6,174,540 | B1 | 1/2001 | Williams et al. |
| 6,239,112 | B1 | 5/2001 | Macy et al. |
| 6,270,768 | B1 | 8/2001 | O'Connell et al. |
| 6,271,255 | B1 | 8/2001 | Leadlay et al. |
| 6,339,063 | B1 | 1/2002 | Kropp et al. |
| 6,437,151 | B2 | 8/2002 | Leadlay et al. |
| 6,472,371 | B1 | 10/2002 | Dirlam et al. |
| 6,514,492 | B1 | 2/2003 | Gao et al. |
| 6,514,945 | B1 | 2/2003 | Boettner |
| 6,733,767 | B2 | 5/2004 | Chern et al. |
| 6,790,867 | B2 | 9/2004 | Kohan et al. |
| 6,825,327 | B2 | 11/2004 | Sklavounos et al. |
| 7,041,670 | B2 | 5/2006 | Boojamra et al. |
| 7,153,842 | B2 | 12/2006 | Hecker et al. |
| 7,361,689 | B2 | 4/2008 | Shuster et al. |
| 7,572,777 | B2 | 8/2009 | Hecker et al. |
| 7,713,950 | B2 | 5/2010 | Shuster et al. |
| 7,786,329 | B2 | 8/2010 | Towson |
| 2002/0102280 | A1 | 8/2002 | Anderson |
| 2003/0216447 | A1 | 11/2003 | Kohan et al. |
| 2004/0242546 | A1 | 12/2004 | Freehauf et al. |
| 2005/0182059 | A1 | 8/2005 | Winzenberg et al. |
| 2005/0182139 | A1 | 8/2005 | Shuster et al. |
| 2006/0063841 | A1 | 3/2006 | Meyer et al. |

(Continued)

FOREIGN PATENT DOCUMENTS

CN 1507858 6/2004

(Continued)

OTHER PUBLICATIONS

Banerjee et al, "Photoreleasable Protecting Groups Based on Electron Transfer Chemistry. Donor Sensitized Release of Phenacyl Groups from Alcohols, Phosphates and Diacids", Tetrahedron, vol. 55, pp. 12699-12710 (1999).
Brunelle, "Novel Chatalysis of o-Nitrophenyl Carbonates by p-Dimethylaminopyridine", Tetrahedron Letters, vol. 23, No. 17, pp. 1739-1742 (1982).
Castro et al, "Kinetic Investigation of the Phenolysis of Phenyl 4-Nitrophenyl and Phenyl 2,4-Dinitrophenyl Carbonates", J. Chem. Soc. Perkin Trans., vol. 2, pp. 2351-2354 (2001).
Chen et al, "Synthesis of (+)-CP-263,114", J. Am. Chem. Soc., vol. 122, pp. 7424-7425 (2000).
Chmielewski et al, "Thermolytic Carbonates for Potential 5'-Hydroxyl Protection of Deoxyribonucleosides", J. Org.Chem., vol. 68, pp. 10003-10012 (2003).

(Continued)

Primary Examiner — Janet Andres
Assistant Examiner — Heidi Reese

(57) ABSTRACT

The present invention discloses certain novel prodrugs of chloramphenicol or thiamphenicol, or of an analog of either, including prodrugs of pharmaceutically acceptable salts of chloramphenicol or thiamphenicol or of their analogs, including nitrogen-containing esters of both alcohol groups of such compounds. In certain embodiments these novel prodrugs are sufficiently water-soluble to serve the functions needed of a prodrug of chloramphenicol or thiamphenicol or of an analog of either. In one embodiment, a certain subclass of the compounds also possesses the hydrolytic stability needed to maintain the prodrug in solution in the subject's system until appropriate conditions exist when the prodrug can hydrolyze, releasing the active compound in question.

6 Claims, No Drawings

U.S. PATENT DOCUMENTS

| | | | |
|---|---|---|---|
| 2006/0128779 A1 | 6/2006 | Winzenberg et al. |
| 2006/0281695 A1 | 12/2006 | Meyer et al. |
| 2007/0055066 A1 | 3/2007 | Towson |
| 2007/0055067 A1 | 3/2007 | Towson |
| 2007/0155799 A1 | 7/2007 | Glinka et al. |
| 2007/0238700 A1 | 10/2007 | Winzenberg et al. |
| 2008/0145317 A1 | 6/2008 | Tongiani et al. |
| 2008/0146640 A1 | 6/2008 | Glinka |
| 2008/0153906 A1 | 6/2008 | Celly et al. |
| 2008/0188556 A1 | 8/2008 | Glinka et al. |
| 2008/0319200 A1 | 12/2008 | Towson |
| 2009/0062397 A1 | 3/2009 | Tongiani |
| 2009/0156683 A1 | 6/2009 | Simmons et al. |
| 2009/0170954 A1 | 7/2009 | Towson et al. |
| 2009/0275662 A1 | 11/2009 | Barbot |
| 2010/0210851 A1 | 8/2010 | Towson |

FOREIGN PATENT DOCUMENTS

| | | |
|---|---|---|
| EP | 0980248 | 10/2001 |
| GB | 804986 | 11/1958 |
| GB | 1173562 | 12/1969 |
| GB | 1263116 | 2/1972 |
| WO | WO 02/41899 | 5/2002 |
| WO | WO 03/097054 | 11/2003 |
| WO | WO 2004/089355 | 10/2004 |

OTHER PUBLICATIONS

Diaz et al, Cal-B-Catalyzed Alkoxycarbonylation of A-Ring Stereoisomeric Synthons of 1α,25-Dihydroxyvitamin $D_3$: A Comparative Study. First Regioselective Chemoenzymatic Synthesis of 19-*nor*-A-Ring Carbonates, J. Org.Chem., vol. 66, pp. 4227-4232 (2001).

Dubowchik et al, "Cathepsin B-Sensitive Dipeptide Prodrugs. 2. Models of Anticancer Drugs Paclitaxel (Taxol®), Mitomycin C and Doxorubicin", Bloorganic & Medicinal Chemistry Letters, vol. 8, pp. 3347-3352 (1998).

Greiner et al, "Synthesis of Phosphoramidite Building Blocks of 2'-Amino-2'deoxyribonucleosides: New Compounds for Oligonucleotide Synthesis", Helvetica Chimica Acta, vol. 81, pp. 1528-1544 (1998).

Harada et al, "Allyloxycarbonyl Group as a Protective Group for the Hydroxyl Group in Carbohydrates", J. Carbohydrate Chemistry, vol. 14, No. 1, pp. 165-170 (1995).

Iimori et al, "A Novel Intramolecular Decarboxylative Glycosylation *via* Mixed Carbonate", Tetrahedron Letters, vol. 37, No. 13, pp. 2267-2270 (1996).

Kenar et al, "Synthesis and Characterization of Dialkyl Carbonates Prepared from Mid-, Long-Chain, and Guerbet Alcohols", J. Am. Oil Chem. Soc., vol. 81, No. 3, pp. 285-291 (2004).

Kozikowski et al, "Novel PI Analogues Selectively Block Activation of the Pro-Survival Serine/Threonine Kinase Akt", J. Am. Chem. Soc., vol. 125, pp. 1144-1145 (2003).

Kryczka et al, "Syntheses de Carbonates et Carbamates Benzyliques et Allyliques", Bull. Soc. Chim. Belg., FR, vol. 101, No. 2, pp. 147-157 (1992).

Li et al, "Synthesis of DNA Oligomers Possessing a Covalently Cross-Linked Watson—Crick Base Pair Model", Angew. Chem. Int. Ed., vol. 113, No. 8, pp. 1519-1523 (2001).

Marca et al, "Observations on Antibacterial Activity of Thiamphenicol Glycinate Acetylcysteinate", Quademi Sclavo di Diagnostica Clinica e di Laboratorio, vol. 15, No. Suppl. 1, pp. 777-784 (Jun. 1979).

Mindl et al, "Alkoxycarbonylation of Alcohols and phenols by Nitrosoformates", Collect Czech. Chem. Commun., vol. 61, pp. 1053-1063 (1996).

Moris et al, "A Novel and Convenient Route to 3'-Carbonates from Unprotected 2'-Deoxynucleosides Through an Enzymatic Reaction", J. Org. Chem., vol. 57, pp. 2490-2492 (1992).

Moris et al, "Enzymatic Acylation and Alkoxycarbonylation of α-, Xylo-, Anhydro-, and Arabino-Nucleosides", Tetrahedron, vol. 49, No. 44, pp. 10089-10098 (1993).

Nongkunsarn et al, Rearrangement and Radical Mediated Decarboxylation of Trimethylsilyl Benzoates Using Xenon Difluoride, J. Chem. Soc. Perkin Trans., vol. 1, No. 2, pp. 121-122 (1996) [Abstract].

Olofson et al, "A Regiospecific and Stereospecific Route to Enol Carbonates and Carbamates: Closer Look at a 'Naked Anion'", Tetrahedron Letters, vol. 21, pp. 819-822, (1980).

Peri et al, "Preparation of Bicyclo[3.2.0]heptane-2-*endo*,7-*endo*-diols:1,3-Diols with a Chiral Riged Backbone", J. Org. Chem., vol. 69, pp. 1353-1356 (2004).

Pulido et al, "Enzymatic Regioselective Alkoxycarbonylation of Hexoses and Pentoses with Carbonate Oxime Esters", J. Chem. Soc. Perkin Trans., vol. 1, pp. 589-592 (1993).

Rege et al, "Chemoenzymatic Synthesis and high-Throughput Screening of an Aminoglycoside-Polyamine Library: Identification of High-Affinity Displacers and DNA-Binding Ligands", J. Am. Chem.Soc., vol. 126, pp. 12306-12315 (2004).

Schirmeister et al, "The 2-(4-Nitrophenyl)ethoxycarbonyl (npeoc) and 2-(2,4-Dinitrophenyl)ethoxycarbonyl (dnpeoc) Groups for Protection of Hydroxy Functions in Ribonucleosides and 2'-Deoxyribonucleosides", Helvetica Chimica Acta, vol. 76, pp. 385-401 (1993).

Shue et al, "Novel Methodology for the Synthesis of *trans*-Alkene Dipeptide Isosteres", J. Org. Chem., vol. 56, pp. 2107-2111 (1991).

Takamizawa et al, "Studies of the Pyrimidine Derivatives. XXV. The Reaction of Alkoxycarbonylthiocyanates and Related Compounds with the Sodium Salt of Thiamine", Bull. Chem. Soc. Jpn., vol. 36, No. 9, pp. 1214-1220 (1963).

Von Dem Bruch et al, "The 3-(3-Pyridyl)allyloxycarbonyl (Paloc) Moiety-a Stable, Amino Protecting Group for Peptide Syntheses in Organic Media and in Water That is Cleavable under Neutral Conditions", Angew. Chem., vol. 102, No. 12, pp. 1520-1522 (1990).

Wang et al, "Solid Phase Synthesis of Neutral Oligonucleotide Analogues", Tetrahedron Letters, vol. 32, No. 50, pp. 7385-7388 (1991).

Weber et al, "Steryl and Stanyl Esters of Fatty Acids by Solvent-Free Esterification and Transesterification in Vacuo Using Lipases from *Rhizomucor miehei, Candida Antarctica*, and *Carica papaya*", J. Agric. Food Chem., vol. 49, pp. 5210-5216 (2001).

Whalen et al, "Resolution of a Chiral Alcohol Through Lipase-Catalyzed Transesterification of its Mixed Carbonate by poly(ethylene glycol) in Organic Media", Tetrahedron: Asymmetry, vol. 11, pp. 1279-1288 (2000).

Wuts et al, "New Process for the Preparation of Methyl Carbonates", Organic Letters, vol. 5, No. 9, pp. 1483-1486 (2003).

Freedom of Information Summary, Original New Animal Drug Application, NADA 141-265 Sponsored by Schering-Plough Animal Health, Approved Mar. 21, 2008.

Nuflor Package Insert, 2003.

Veterinary Pharmaceuticals and Biologicals, The Veterinarian's PDR, Veterinary Medicien Publishing Group, pp. 652 (1997-1998).

International Search Report for Corresponding PCT/US2007/025319, mailed May 29, 2008.

WATER-SOLUBLE PRODRUGS OF CHLORAMPHENICOL, THIAMPHENICOL, AND ANALOGS THEREOF

CROSS-REFERENCE TO RELATED APPLICATIONS

This application is a non-provisional application that claims priority under 35 U.S.C. §119(e) of provisional application U.S. Ser. No. 60/874,860 filed Dec. 13, 2006, the contents of which are hereby incorporated by reference in its entirety.

FIELD OF THE INVENTION

This invention relates to new prodrugs of certain phenicols, and, in some embodiments, to certain charged nitrogen-containing esters and carbonates of chloramphenicol, thiamphenicol, and analogs thereof that demonstrate improved water solubility and hydrolytic stability.

BACKGROUND OF THE INVENTION

Chloramphenicol, 2.2-dichloro-N [2-hydroxy-1-(hydroxymethyl)-2-(4-nitrophenyl)ethyl]acetamide is a broad based antibiotic that has long been known to inhibit protein synthesis in both gram positive and gram negative bacteria. Presently in disfavor in a number of developed countries for use in humans and food animals, due to its association in with aplastic anemia in humans, chloramphenicol continues to be employed, for treating companion animals worldwide, and livestock in developing countries. A close structural analogue, thiamphenicol, D-threo-2,2-dichloro-N-[β-hydroxy-α-(hydroxymethyl)-p-methylsulfonyl)phenethyl]acetamide, see structures below, has a similar broad spectrum of activity, but has never been associated with aplastic anemia. Chloramphenicol and thiamphenicol have the chemical formulas

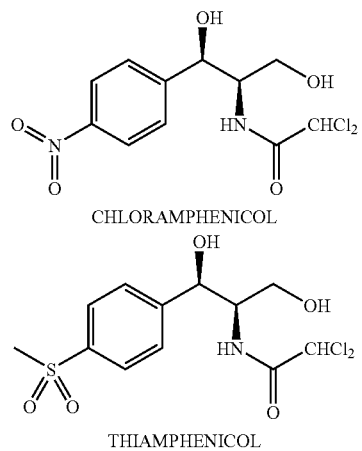

Thiamphenicol is currently used worldwide to treat animals with bacterial infections, and is currently used in the treatment of humans in China. Also known in the art are analogs of these compounds having substituents other than nitro and methylsulfonyl, for example compounds in which the 4-substituent on the phenyl ring is selected from

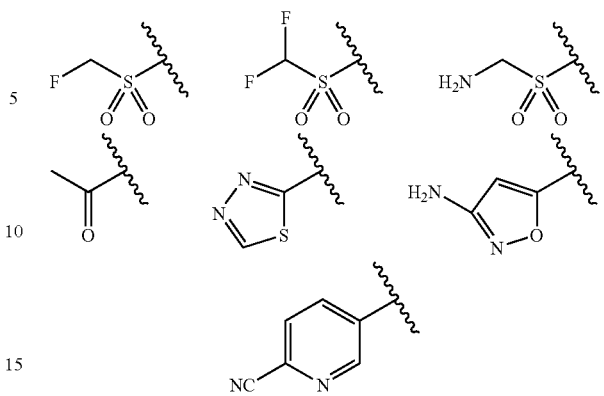

As stated above, chloramphenicol and thiamphenicol have broad spectrum antibiotic activity against many gram-negative and gram-positive bacteria, including utility in the prevention and treatment of bacterial infections due to susceptible pathogens in birds, reptiles, fish, shellfish and mammals. Examples of susceptible organisms include: *Mannheimia haemolytica, Pasteurella multocida, Haemophilus somnus*, also known as *Histophilus somni, Fusobacterium necrophorum, Bacterioides melaninogenicus, Actinobacillus pleuropneumoniae, Streptococcus suis, Salmonella cholerasuis, Mycoplasma* spp., *Escherichia coli; Edwardsiella ictaluri, Aeromonas salmonicida, Enterobacter, Klebsiella, Staphylococcus, Enterococcus, Bordetella, Proteus, Shigella, K. pneumoniae, E. cloacae*, and *S. typhus*.

Given the need for economical, single-dose treatment in the veterinary setting, there remains a need for new formulations of chloramphenicol and/or thiamphenicol at high concentrations. In addition, there is also a need for forms of chloramphenicol and thiamphenicol that are capable of maintaining effective plasma antibiotic levels for prolonged periods of time, in order to achieve improved economies in administration, e.g., to more readily provide single dose treatment, particularly in a veterinary setting. In addition there is a need for similar forms of chloramphenicol and thiamphenicol analogs.

One of the important applications is a treatment of bacterial infections by dosing the drug in drinking water given to animals. Such means of administration provides effective treatment of bacterial infection since chloramphenicol and thiamphenicol are reasonably well absorbed from the intestine ad achieves necessary antibacterial systemic levels. However, as mentioned above, the aqueous solubility of these compounds is quite limited; consequently their solubilization in water is slow. Achieving the desired concentrations in drinking water requires preparation of pre-dissolved chloramphenicol or thiamphenicol in the form of a concentrate in a water-miscible organic solvent. Additionally, a water-soluble prodrug of either compound or of an analog of either that was easily dissolved directly in the drinking water for animals would be quite desirable.

Known in the prior art are water-soluble prodrugs of these two antibiotics produced by esterification of the relatively easily accessible primary alcohol group. Glycinates of these compounds have been extensively investigated, for example. Some examples of such esters are disclosed in U.S. Pat. Nos. 3,740,411 and 3,770,889 (both of Akiyama et al.). British patent 1,263,116 of Sumitomo Chemical Co., and 3,405,165 and 3,475,470 (both of Rebstock et al.). However, there still remains a need for alternative forms of chloramphenicol or thiamphenicol that have additional beneficial features.

A provisional patent application, U.S. Ser. No. 60/874,864 filed Dec. 13, 2006, drawn to analogous florfenicol prodrugs was filed with the U.S. Patent and Trademark Office on the same day as the provisional application from which the present application claims priority. It also should be noted that the citation of any reference herein should not be construed that such reference is available as "prior art" to the instant Application.

BRIEF SUMMARY OF THE INVENTION

In brief, this invention comprises certain novel prodrugs of chloramphenicol or thiamphenicol, or of an analog of either, as described herein, including prodrugs of pharmaceutically acceptable salts of chloramphenicol or thiamphenicol or of their analogs. These prodrugs comprise nitrogen-containing esters of both alcohol groups of such compounds and, in certain embodiments, are sufficiently water-soluble to serve the functions needed of a prodrug of chloramphenicol or thiamphenicol or of an analog of either. In one embodiment, a certain subclass of the compounds also possesses the hydrolytic stability needed to maintain the prodrug in solution in the subject's system until appropriate conditions exist when the prodrug can hydrolyze, releasing the active compound in question.

Other aspects of the invention comprise pharmaceutical formulations of the above-mentioned prodrugs, or of their pharmaceutically acceptable salts, also comprising one or more pharmaceutically acceptable excipients or carriers. Still other aspects comprise a method for treating a subject with chloramphenicol or thiamphenicol or an analog of either comprising administering to said subject an effective amount of a prodrug, of chloramphenicol or thiamphenicol or an analog of either, or of a pharmaceutically acceptable salt of these, or a pharmaceutical composition containing the same, according to this invention.

The present invention further provides pharmaceutical compositions that comprise prophylactically-effective amounts of one or more novel prodrugs of chloramphenicol and/or of thiamphenicol and/or one or more analogs of either, and/or pharmaceutically acceptable salts of any of these. In addition, in certain pharmaceutical compositions, chloramphenicol and/or thiamphenicol, and/or florfenicol also may be included in combination. In addition, the present invention also provides pharmaceutical compositions that comprise such novel prodrugs that are useful for metaphylaxis. The pharmaceutical compositions of the present invention can be administered to animals or fish in prophylactically-effective amounts, and/or for metaphylaxis, as a need and/or the practice merits. Corresponding methods of administering prophylactically-effective amounts of the pharmaceutical compositions of the present invention and/or for metaphylaxis, as a need and/or the practice merits, are also provided by the present invention. The present invention also provides methods of treating or preventing a disease or disorder in an animal in need thereof.

DETAILED DESCRIPTION OF THE INVENTION

The present invention provides novel prodrugs of chloramphenicol or thiamphenicol, or of their analogs, including prodrugs of pharmaceutically acceptable salts of chloramphenicol or thiamphenicol or of their analogs. These prodrugs possess one or more advantageous properties such as: water solubility, hydrolytic stability in aqueous systems, and/or the ability to become released in the gastric tract of the animal due to enzymatic action. In particular embodiments, the prodrug is not converted to the parent drug prematurely either in the dosing solution and/or in the intestine (when intended to be used for the improvement of oral absorption). In a more particular embodiment, the administration of a prodrug of the present invention to a subject produces the desired rate of the conversion to the parent drug when the prodrug reaches its intended destination.

Thus, a prodrug molecule containing a moiety that results in improvement in solubility but is not sufficiently chemically stable when dissolved may not achieve the desired effect.

If the parent drug is acceptably well absorbed from the gastrointestinal system then the intended effect of the prodrug may be simply the improved solubility in order to facilitate the administration (e.g., in drinking water) In such case the release of the parent drug in the gastric system from the prodrug may occur by one or both of two independent mechanisms: enzymatic hydrolysis due to the action of an intestinal enzyme or chemical hydrolysis triggered by increase of pH encountered in the intestine relative to the pH of the original dosing solution. The chemical release of the parent drug may be due to the hydrolysis of the ester bond facilitated by elevated pH or by the action of some prodrug moieties capable of intramolecular cyclization. Specifically, the parent drug release may be due to the intramolecular displacement of the parent drug by the primary or secondary amine of the prodrug triggered by the pH change.

Accordingly, the invention provides novel prodrugs of chloramphenicol or thiamphenicol and/or analogs of either, having the Formula (I) and pharmaceutically acceptable salts thereof:

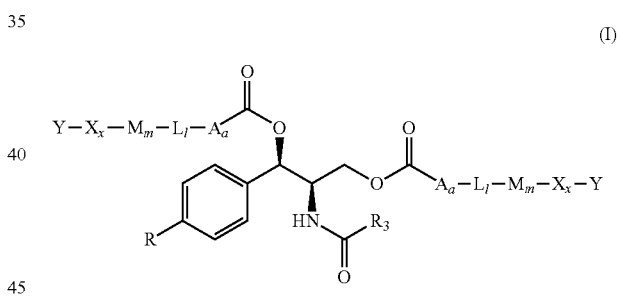

in which:

R is selected from the group consisting of

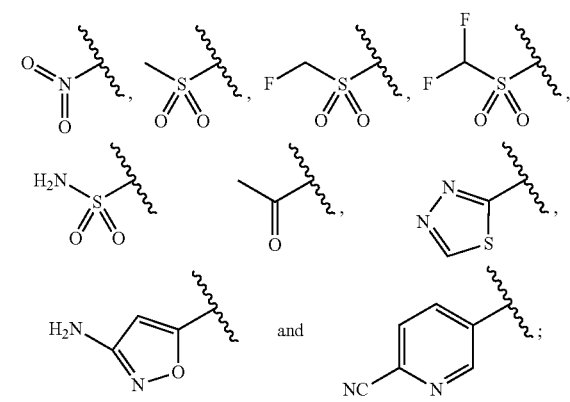

A is oxygen and a is zero or 1,

L is: (a) $CH_2$ and l is an integer from 1 to 6;
 (b) $CHR_1$ where $R_1$ is an amino acid side chain and l is 1; or
 (c) $CHR_1NHC(O)CH(NH_2)R_2$ where $R_1$ and $R_2$ are amino acid side chains and l is 1;

M is: (a) oxygen or sulfur and m is zero or one;
 (b) $CH_2$ and m is zero or an integer from 1 to 4; or
 (c) NH and m is 1;

X is: (a) $CH_2$ and x is zero or an integer from 1 to 4; or
 (b) C(O) and x is 1; and Y is: (a) $NH_2$;
 (b) $NHR_x$, where $R_x$ is methyl, ethyl, n-propyl or isopropyl;
 (c) $NR_yR_z$ where $R_y$ and $R_z$ are independently hydrogen, methyl, ethyl, n-propyl or isopropyl, or $R_y$ and $R_z$ taken together form a $C_2$-$C_5$ alkylene chain, or a $C_2$-$C_4$ alkylene chain further including a nitrogen or oxygen heteroatom in said chain;
 (d) $C(=NH)NH_2$;
 (e) $N^+R_4R_5R_6$ where $R_4$, $R_5$, and $R_6$ are independently hydrogen, methyl or ethyl or $R_4$ and $R_5$ taken together form a $C_2$-$C_5$ alkylene chain, or a $C_2$-$C_4$ alkylene chain further including a nitrogen or oxygen heteroatom in said chain;
 (f) pyridinium;
 (g) N-methyl or N-ethyl pyridinium;
 (h) N'-3-methyl-N-1-imidazolium;
 (i) a phenyl group substituted by a group having the formula $NR_4R_5$ or $N^+R_4R_5R_6$ where $R_4$, $R_5$, and $R_6$ are as defined above; or
 (j) $NH-CR_7(=NH)$ where $R_7$ is hydrogen, methyl or amino; and $R_3$ is selected from the group consisting of dichloromethyl, difluoromethyl, chlorofluoromethyl, chloromethyl, methyl, cyanomethyl, azidomethyl, and aminomethyl.

In a particular embodiment of these compounds, the nitrogen atom of a prodrug moiety is a charged atom. Furthermore, in order to modulate the rate of hydrolysis of ester promoieties containing such a charged nitrogen atom or a sufficiently basic nitrogen atom assuring that the prodrug exists predominantly in charged form at the physiological pH, the nitrogen atom can be placed at a distance away from the carbonyl bond of the ester. The same effect can be achieved in carbonate derivatives containing a charged nitrogen atom by attaching the charged nitrogen atom further away from the hydrolyzable carbonate functionality. A charged nitrogen atom distance of at least two atoms, or at least three atoms, away from the carbonyl carbon atom of the ester or carbonate group to be hydrolyzed in the release of the parent drug is satisfactory for achieving the desired hydrolytic stability of the ester or carbonate.

Some preferred compounds of this invention include those in which R is nitro or methylsulfonyl and $R_4$ is hydroxymethyl and their pharmaceutically acceptable salts. In some preferred compounds the two groups $A_a$-$L_l$-$M_m$-$X_x$—Y are identical; in others they may be different.

Other preferred compounds are those of Formula (I) in which Y includes a positively charged nitrogen atom, i.e., Y is a group $N^+R_4R_5R_6$ where $R_4$, $R_5$, and $R_6$ are independently hydrogen, methyl or ethyl such as $NH_3^+$, $N^+H_2CH_3$ or $N^+(CH_3)_3$. Compounds in which a is zero are esters; those in which a is 1 are carbonates.

Compounds of Formula (I) include compounds in which the group
$A_a$-$L_l$-$M_m$-$X_x$—Y is, for instance as shown below:

1. Dipeptide esters R=H, aminoacid sidechain

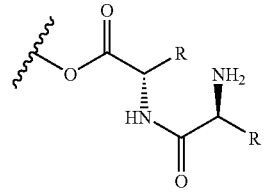

2. Omega amino esters (n=2-6) R=H, Me, Et

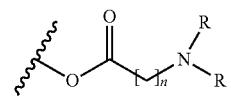

3. Omega amidino esters N-linked (n=2-6) R=H, Me

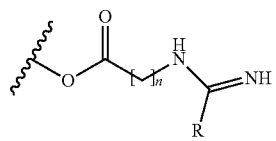

4. Omega amidino esters, C-linked (n=2-6)

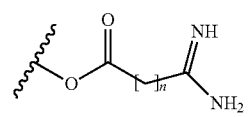

5. Omega guanidine esters (n=2-6)

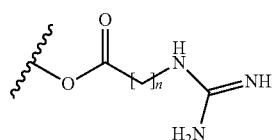

6. Omega amino acid esters-cyclic amines ($n_1$=1-6; $n_2$=2-4

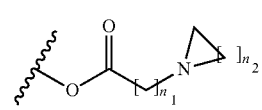

7. Omega quaternary ammonium esters (n=1-6) R=Me, Et

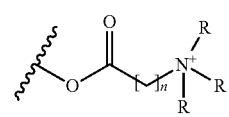

8. Omega quaternary ammonium esters-cyclic amines ($n_1$=1-6; $n_2$=2-4: R=Me, Et)

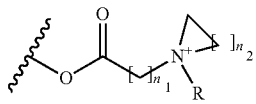

9. Omega quaternary ammonium esters-cyclic diamines (n=2-6; R=H, Me, Et)

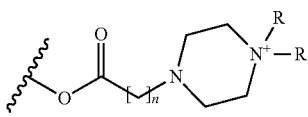

10. Omega pyridinium salts, C-linked; (n=2-6; R=Me, Et)

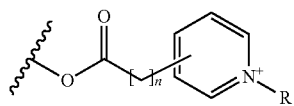

11. Omega imidazolium salts (n=2-6; R=Me, Et)

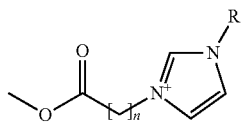

12. Aminomethyl benzoates R=Me, Et

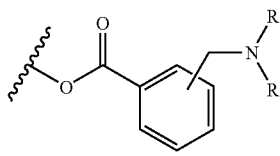

13. Quaternary salts of aminomethyl benzoates R=Me, Et

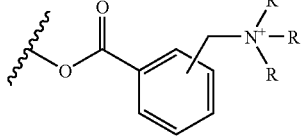

For types 2-11, also

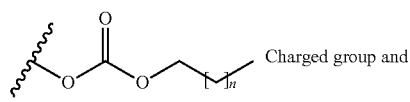

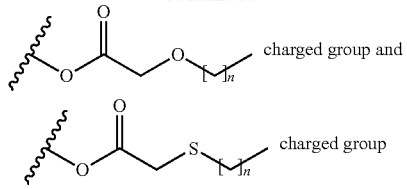

versions, where "charged group" represents a positively charged nitrogen-containing moiety of the type indicated.

Compounds of Formula (I) include in general, and as exemplified below:

A. Carbonates with a terminal amine functionality

B. Esters with an additional alpha-heteroatom (O, S) in the linker; for instance—

$COCH_2OCH_2CH_2NH_2$ or $C(O)CH_2SCH_2CH_2NH_2$

C. Esters with an additional alpha-heteroatom (N)—which are amino acid derivatives but do not bear a protonable amine at the alpha position; these are dipeptides—for example—

—$C(O)CH_2NHCOCH_2NH_2$ and —$C(O)CH(Me)NHCOCH(Me)NH_2$

D. Esters with quaternary nitrogen atoms removed at least two methylene groups away from the carbonyl group, for example $C(O)CH_2CH_2CH_2$—N-methylimidazolium and $C(O)CH_2CH_2CH_2N^+Me_3$.

In another aspect, this invention relates to processes for preparing the novel compounds. In one process, compounds of the invention that are esters may be prepared by reacting chloramphenicol or thiamphenicol or an analog of either with a carboxylic acid or a derivative thereof having a terminal group W which represents a protected primary or secondary amine that is later deprotected to a free amine, a tertiary amine, or a group that is later manipulated into a required charged nitrogen functionality. A commercially available activated derivative of the carboxylic acid may be used for the formation of the ester; it may be prepared in a separate reaction step or it may be prepared in situ in presence of chloramphenicol or thiamphenicol, or analog

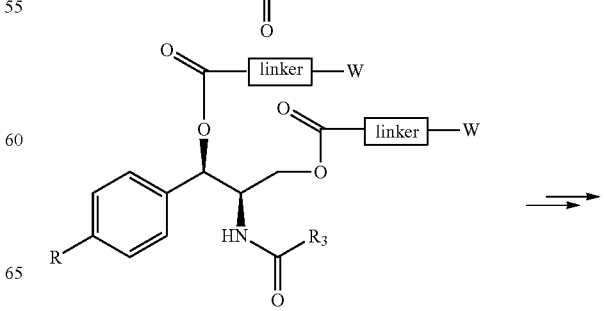

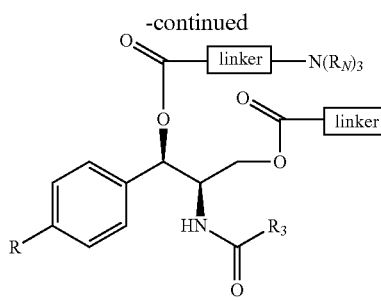

Compounds of the invention that are carbonates are prepared by reacting the chloramphenicol or thiamphenicol, or analog thereof, with a derivative of an alkoxycarbonic acid, for example a chloroformate having a terminal group W which represents a protected primary or secondary amine that is later deprotected to a free amine, a tertiary amine, or a group that is later manipulated into a required charged nitrogen functionality:

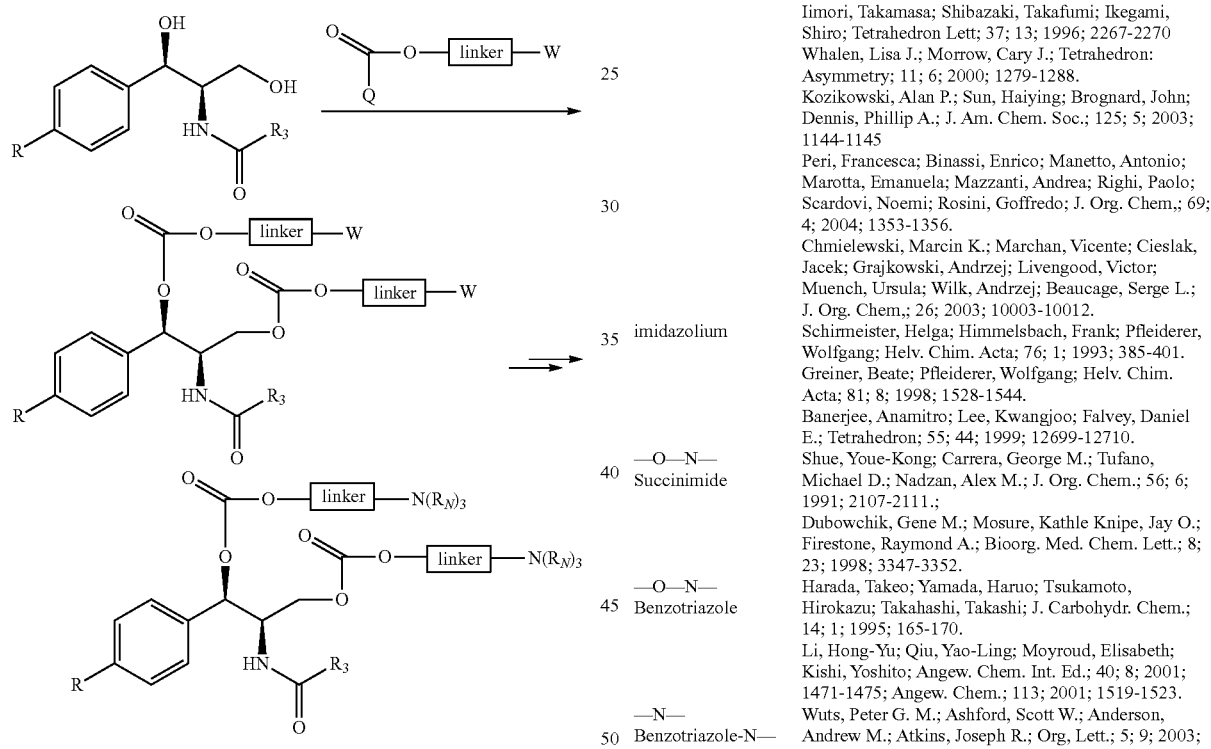

The necessary acids or chloroformates, if not commercially available, can readily be prepared by methods known to those in the art. Appropriate reaction conditions, solvents, etc., are exemplified below.

As shown in the above reaction schemes both alcohol functionalities of chloramphenicol or thiamphenicol or an analog of either are reacted with the activated carboxylic acid or alkoxy carbonic acid reagents having the nucleophilic displacement of group Q. Most common reagents of this type utilize Q=chlorine but many other leaving groups known in the art may be also employed.

As alternative to chloroformates (Q=chlorine), other reagents with different leaving groups Q may be used for preparation of carbonates. Representative references are cited for each leaving group, each incorporated by reference herein.

| Value of Q | References |
|---|---|
| —F | Olofson, R. A.; Cuomo, John; Tetrahedron Lett.; 21; 1980; 819-822; Nongkunsarn, Pakawan; Ramsden, Christopher A.; J. Chem. Soc. Perkin Trans, 1; 2; 1996; 121-122. |
| —CN | Adickes et al; J. Prakt. Chem.; 2; 133; 1932; 313. Cen, Chuo; Layton, Mark E.; Sheehan, Scott M.; Shair, Matthew D.; J. Am, Chem, Soc.; 122; 30; 2000; 7424-7425. |
| —SCN | Takamizawa, A. et al; Bull. Chem. Soc. Jpn.; 36; 9; 1963; 1214-1220. |
| —NCS | Takamizawa, A. et al; Bull. Chem. Soc. Jpn.; 36; 9; 1963; 1214-1220. |
| —O-aryl or —O-aryl | Patent; Chininfabr. Zimmer & Co.; DE 117095. Weber, Nikolaus; Wetkamp, Petra; Mukherjee, Kumar D.; J. Agric. Food Chem.; 49; 11; 2001; 5210-5216. Kenar, James A.; Knothe, Gerhard; Copes, Ashley L.; J. Am. Oil Chem. Soc.; 81; 3; 2004; 285-291. |
| —NH—OH | Mindl, Jaromir; Halama, Ales; Cernosek, Zdenek; Collect. Czech. Chem. Commun.; 61; 7; 1996; 1053-1063. |
| imidazole | Kryczka, Boguslaw; Bull. Soc. Chim. Belg.; FR; 101; 2; 1992; 147-158. Iimori, Takamasa; Shibazaki, Takafumi; Ikegami, Shiro; Tetrahedron Lett; 37; 13; 1996; 2267-2270 Whalen, Lisa J.; Morrow, Cary J.; Tetrahedron: Asymmetry; 11; 6; 2000; 1279-1288. Kozikowski, Alan P.; Sun, Haiying; Brognard, John; Dennis, Phillip A.; J. Am. Chem. Soc.; 125; 5; 2003; 1144-1145 Peri, Francesca; Binassi, Enrico; Manetto, Antonio; Marotta, Emanuela; Mazzanti, Andrea; Righi, Paolo; Scardovi, Noemi; Rosini, Goffredo; J. Org. Chem,; 69; 4; 2004; 1353-1356. Chmielewski, Marcin K.; Marchan, Vicente; Cieslak, Jacek; Grajkowski, Andrzej; Livengood, Victor; Muench, Ursula; Wilk, Andrzej; Beaucage, Serge L.; J. Org. Chem,; 26; 2003; 10003-10012. |
| imidazolium | Schirmeister, Helga; Himmelsbach, Frank; Pfleiderer, Wolfgang; Helv. Chim. Acta; 76; 1; 1993; 385-401. Greiner, Beate; Pfleiderer, Wolfgang; Helv. Chim. Acta; 81; 8; 1998; 1528-1544. Banerjee, Anamitro; Lee, Kwangjoo; Falvey, Daniel E.; Tetrahedron; 55; 44; 1999; 12699-12710. |
| —O—N— Succinimide | Shue, Youe-Kong; Carrera, George M.; Tufano, Michael D.; Nadzan, Alex M.; J. Org. Chem.; 56; 6; 1991; 2107-2111.; Dubowchik, Gene M.; Mosure, Kathle Knipe, Jay O.; Firestone, Raymond A.; Bioorg. Med. Chem. Lett.; 8; 23; 1998; 3347-3352. |
| —O—N— Benzotriazole | Harada, Takeo; Yamada, Haruo; Tsukamoto, Hirokazu; Takahashi, Takashi; J. Carbohydr. Chem.; 14; 1; 1995; 165-170. Li, Hong-Yu; Qiu, Yao-Ling; Moyroud, Elisabeth; Kishi, Yoshito; Angew. Chem. Int. Ed.; 40; 8; 2001; 1471-1475; Angew. Chem.; 113; 2001; 1519-1523. |
| —N— Benzotriazole-N— oxide | Wuts, Peter G. M.; Ashford, Scott W.; Anderson, Andrew M.; Atkins, Joseph R.; Org, Lett.; 5; 9; 2003; 1483-1486. |
| —O—N=CR$_2$ | Pulido, Rosalino; Gotor, Vicente; J. Chem. Soc. Perkin Trans. 1; 5; 1993; 589-592. Moris, Franciso; Gotor, Vicente; J. Org. Chem.; 57; 8; 1992; 2490-2492. Moris, Francisco; Gotor, Vicente; Tetrahedron; 49; 44; 1993; 10089-10098, Diaz, Monica; Gotor-Fernandez, Vicente; Ferrero, Miguel; Fernandez, Susana; Gotor, Vicente; J. Org. Chem.; 66; 12; 2001; 4227-4232. Rege, Kaushal; Hu, Shanghui; Moore, James A.; Dordick, Jonathan S.; Cramer, Steven M.; J. Am. Chem. Soc.; 126; 39; 2004; 12306-12315. |
| Ortho- or para-nitrophenol | Brunelle, Daniel J.; Tetrahedron Lett.; 23; 17; 1982; 1739-1742. Bruch, Karsten von dem; Kunz, Horst; Angew. Chem.; 102; 12; 1990; 1520-1522. Wang, Haiyan; Weller, Dwight D.; Tetrahedron Lett.; 32; 50; 1991; 7385-7388. |

| Value of Q | References |
|---|---|
| 2,4-dinitrophenol | Iimori, Takamasa; Shibazaki, Takafumi; Ikegami, Shiro; Tetrahedron Lett; 37; 13; 1996; 2267-2270. Castro, Enrique A.; Angel, Mauricio; Pavez, Paulina; Santos, Jose G.; J. Chem. Soc. Perkin Trans. 2; 12; 2001; 2351-2354. |

The reaction may be facilitated by the addition of a catalyst like a trialkylamine, pyridine, a 4-alkylpyridine, a 4-diaminoalkyl pyridine or a combination thereof. Formation of the initial ester or carbonate intermediate can be conveniently performed in a variety of solvents. Suitable solvents include, for example, chlorinated solvents such as dichloromethane and 1,2-dichloroethane; ester solvents such as ethyl acetate, isopropyl acetate, isoamyl acetate, ethylene glycol diacetate, propylene glycol diacetate, glycerol triacetate; monoether solvents such as diethyl ether, diisopropyl ether, methyl tert-butyl ether; polyether solvents such as ethylene glycol ethers, dimethyl ethylene glycol ether, diethylene glycol ethers: diethylene glycol dimethyl ether, diethylene glycol diethyl ether; formaldehyde acetal ethers such as dimethoxymethane, diethoxymethane, dibutoxymethane; cyclic ethers such as tetrahydrofuran, 1,3-dioxolane, 1,4-dioxane; ketone solvents such as acetone, methyl ethyl ketone, methyl isobutyl ketone; mixed ether/ester solvents as represented by monoethers of ethylene and diethylene glycol such as 2-methoxyethyl acetate, 2-ethoxyethyl acetate, 2-(methoxy-ethoxy)ethyl acetate, and 2-(ethoxy-ethoxy)ethyl acetate.

DEFINITIONS

As used herein:

"About" generally signifies that a value is within twenty percent of the indicated value, unless otherwise indicated "Amino acid" refers to the known natural alpha-amino acids, especially those selected from alanine, cysteine, phenylalanine, glycine, histidine, isoleucine, lysine, leucine, methionine, asparagine proline, glutamine, arginine, serine, threonine, valine, tryptophan, and tyrosine. "Amino acid side chain" and "amino acid residue" refer to a group derived from an alpha-amino acid and represents the $R_{aa}$ group in the NH2-CH($R_{aa}$)CO$_2$H structure of the amino acid, for example —CH(CH$_3$)$_2$ for valine, —CH$_2$CH$_2$CH$_2$CH$_2$NH$_2$ for lysine and —CO$_2$OH for serine. For proline it represents —CH$_2$CH$_2$CH$_2$— which has its distal end attached to the alpha nitrogen atom. The term "alpha-N-unfunctionalized" refers to an amino acid residue with an unsubstituted —NH$_2$ group in the alpha position, as opposed to functionalized residues, in which for instance the alpha-amino group is a part of an amide bond of a peptide.

"Alkyl" refers to a straight or branched chain saturated hydrocarbon moiety having the number of carbon atoms designated (i.e. $C_1$-$C_{10}$ means one to ten carbons). Examples of alkyl groups include methyl, ethyl, n-propyl, isopropyl, n-butyl, t-butyl, isobutyl, sec-butyl, and the various pentyl, hexyl, heptyl, octyl, etc. groups. Alkyl groups also include those having one or more heteroatoms in the chain, e.g. methoxymethyl (CH$_3$OCH$_2$—), ethoxyethyl, methylthiomethyl (CH$_3$SCH$_2$—), methylaminomethyl (CH$_3$NHCH$_2$—) and the like.

"Alkylene chain" refers to a divalent hydrocarbyl group derived from an alkyl group, i.e., a saturated straight or branched chain hydrocarbyl group linked at both of its ends to the remainder of the molecule in question. Typical alkylene groups include methylene, —CH$_2$—, ethylene, —CH$_2$CH$_2$— and n-propylene, —CH$_2$CH$_2$CH$_2$—. As with the alkyl groups, alkylene chains can include one or more hetero atoms, e.g., —CH$_2$CH$_2$—NH—CH$_2$CH$_2$—When an alkylene chain is combined with a nitrogen atom, as in groups having the formula NR$_y$R$_z$ the overall group is a heterocyclic group such as a piperidinyl, etc group. When the alkylene chain also includes a heteroatom, the resulting group NR$_y$R$_z$ would be, for instance, a cyclic moiety containing two nitrogen atoms such as a piperidinyl group.

"Prodrug" denotes a compound that is a drug precursor which, upon administration to a subject, undergoes chemical conversion by metabolic or chemical processes to yield the active drug, e.g., a carbonate of chloramphenicol or thiamphenicol or an analog of either is a prodrug that releases the parent compound in vivo.

"Pharmaceutical composition" refers to a composition or formulation comprising a compound according to this invention, including pharmaceutically salts thereof, (e.g., a prodrug of chloramphenicol, thiamphenicol or an analog of either) with a pharmaceutically acceptable excipient and/or carrier. In a particular embodiment the carrier is a solvent (e.g., water).

"Excipient" refers to an inert substance added to a pharmacological composition to further facilitate administration of an active ingredient. Examples without limitation, of excipients include calcium carbonate, calcium phosphate, various sugars and types of starch, celluose derivatives, gelatin, vegetable oils and polyethylene glycols.

"Administer" or "administration" refers to the delivery of the compound or solvate of the present invention or of a pharmaceutical composition containing a compound of this invention to an organism for the purpose of treating or preventing a microbial infection.

"Therapeutically-effective amount," as used herein, refers to that amount of a prodrug of the present invention that will hydrolyze sufficiently rapidly and in sufficient amounts to provide chloramphenicol or thiamphenicol, or an analog of either, in a concentration at which it can relieve to some extent one or more of the symptoms of a bacterial infection in a subject. In particular embodiment, a therapeutically-effective amount refers to that amount of a prodrug of the present invention that, when administered to a subject, delivers the parent compound to a subject in a sufficient plasma concentration to: (1) reduce, and preferably eliminate, the population of bacterial cells in a subject's body; (2) inhibit (i.e., slow, or preferably stop) proliferation of the bacterial cells; (3) inhibit (i.e. slow, preferably stop) spread of the bacterial infection; and/or (4) relieve (preferably eliminate) one or more symptoms associated with the infection.

"Analogs of chloramphenicol or thiamphenicol" refers to analogs of the compound in question having a substituent other than nitro or methylsulfonyl, respectively, on the phenyl ring, as indicated by the designation "R" in Formula (1) or the acetamide group C(O)R$_3$ being other than C(O)CHCl$_2$ "Prophylactically effective amount" refers to the amount of a prodrug of chloramphenicol or thiamphenicol or an analog of either, of the present invention, that provides, upon hydrolysis, a sufficient plasma concentration of the parent compound to: (1) maintain a reduced level of a population of bacterial cells achieved by a previously-administered therapeutically-effective amount of the prodrug or some other appropriate drug; (2) maintain the level of inhibition of the proliferation of bacterial cells achieved by administration of a therapeutically-effective amount of a drug; (3) maintain the degree of inhibition of the spread of the infection achieved by a therapeutically-effective amount of a drug; and/or (4) maintain the level of relief of one or more symptoms, or if symptoms were eliminated, maintain the non-existence of symptoms associated with a bacterial infection achieved by administration of a therapeutically-effective amount of a prodrug (e.g., a prodrug of chloramphenicol) of the present invention or some other appropriate drug. A prophylactically-effective amount also refers to that amount of a composition comprising a prodrug of chloramphenicol or thiamphenicol or an analog of either, of the present invention, that will deliver the parent compound in a sufficient plasma concentration to prohibit bacteria from accumulating in a susceptible organism in sufficient quantity to cause an infection.

Metaphylaxis is the timely mass medication of an entire group of animals to eliminate or minimize an expected outbreak of disease, e.g. in one or more animals at high risk of infection. In one particular embodiment, high risk calves are light weight, commingled with long haul cattle with unknown health histories.

As used herein the term "Minimum Inhibitory Concentration" is used interchangeably with "MIC". An "$MIC_{50}$" is the concentration of the compound (e.g., the prodrug of the present invention) at which the growth of 50% of the isolates is inhibited. Similarly, "$MIC_{90}$" is the concentration of the compound at which the growth of 90% of the isolates is inhibited.

"Subject" refers to an animal species or fish capable of being infected by a pathogenic bacterium, and in a particular embodiment includes humans. Appropriate animal subjects also include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment a "subject" of the invention is a "food producing" animal. For purposes of the present invention, the term "food-producing" animal shall be understood to include all animals bred for consumption or for consumables (e.g. dairy cows egg-laying hens and the like) by humans and/or other animals. A non-limiting list of such animals include avian (chickens, turkeys, geese, duck, ostriches, etc.), bovines (e.g., cattle, dairy cows, buffalo), ovines (e.g., goats or sheep), porcines (e.g., hogs or pigs), equines (e.g., horses) etc., as well as aquatic animals including shellfish and fish such as trout or salmon, and other species raised or harvested for human consumption. For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed *Plecostomus* (*Plecostomus* spp).

In another embodiment, the subject is a companion animal. For purposes of the present invention, the term "companion" animal shall be understood to include housecats (feline), dogs (canine), rabbit species, horses (equine) rodents (e.g., guinea pigs, squirrels, rats, mice, gerbils, and hamsters), primates (e.g., monkeys) and avians, such as pigeons, doves, parrots, parakeets, macaws, canaries, and the like.

Other animals are also contemplated to benefit from the prodrugs of the present invention, including marsupials (such as kangaroos), reptiles (such as farmed turtles), game birds, swans, ratites and other economically important domestic animals.

Pharmaceutically acceptable salts of the compounds described above include hydrochloride, hydrobromide, methanesulfonate, sulfate, 2-hydroxyethylsulfate, citrate, and phosphate.

Pharmaceutical Compositions

A compound of the present invention, or a physiologically acceptable solvate of the compound, may be administered as such to an animal in need thereof, or may be administered in pharmaceutical compositions in which the foregoing materials are mixed with suitable excipient(s) or carriers. Techniques for formulation and administration of drugs may be found in *Remington's Pharmacological Sciences*, Mack Publishing Co., Easton, Pa., latest edition. The formulations and techniques discussed in Remington relate primarily to use with human patients; however, they readily may be modified for use with non-human patients by techniques well-known to those skilled in the veterinary art, Pharmaceutical compositions containing the novel compounds of this invention may also contain typical pharmaceutical excipients and additives such as liquid and/or solid carriers, surface-active agents, dispersants, taste-masking agents, odor-masking agents, and the like. Taste-masking agents include, for instance, those described for quinolones or their derivatives in U.S. Pat. No. 6,514,492 of Gao et al. (which is hereby incorporated by reference herein in its entirety), namely ion exchange resins (including both cationic and anionic resins) such as methacrylic acid-devinylbenzene copolymers (e.g., AMBERLITE® IRP-64), sodium polystyrene sulfonate resins (e.g., AMBERLITE® IRP-69), ad polystyrene sulfonic acid—divinylbenzene resins (e.g., DOWEX® resins).

When the inventive compounds described herein are administered as a component of the feed of the animals, or dissolved or suspended in the drinking water, compositions are provided in which the active agent(s) are intimately dispersed in an inert carrier or diluent. An inert carrier is one that will not react with the inventive compound and one that may be administered safely to animals. Preferably, a carrier for feed administration is one that is, or may be, an ingredient of the animal ration.

Suitable compositions include feed pre-mixes or supplements in which the active ingredient is present in relatively large amounts and which are suitable for direct feeding to the animal or for addition to the feed either directly or after an intermediate dilution or blending step. Typical carriers or diluents suitable for such compositions include for example, distillers' dried gains, corn meal, citrus meal, fermentation residues, ground oyster shells, wheat shorts, molasses solubles, corn cob meal, edible bean mill feed, soya grits crushed limestone, and the like. The inventive compound is intimately dispersed throughout the carrier by methods such as grinding, stirring, milling or tumbling. Compositions containing from about 0.05 to about 5.0% or, more broadly, from about 0.005 to about 2.0% by weight (w/w) of the inventive compounds are particularly suitable as feed pre-mixes. Feed supplements, which are fed directly to the animal, will contain from about 0.0002 to 0.3% by weight of the inventive compound.

Such supplements are added to the animal feed in an amount to give the finished feed the concentration of active compound desired for the treatment and control of susceptible microorganism-s. Although the desired concentration of the inventive compound will vary depending upon the factors mentioned supra as well as upon the particular derivative employed, the compound is usually fed at concentrations of between about 0.0001 to 0.02% of from about 0.00001 to about 0.002% (both values as w/w) in the feed in order to achieve the desired antimicrobial result.

Pharmaceutical compositions of the present invention may be manufactured by processes well known in the art e.g., using a variety of well-known mixing, dissolving, granulating, dragee-making, levigating, emulsifying, encapsulating, entrapping, or lyophilizing process. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramuscular and subcutaneous injection, the compounds of the invention may be formulated in polar solvents including, without limitation, propylene glycol, alcohols, such as benzyl alcohol or ethanol, polyethylene glycol, and N-methyl-2-pyrrolidone, 2-pyrrolidone, other pyrrolidones, N,N-dimethylacetamide, N,N-dimethylformamide, dimethylsulfoxide, acetone, triacetin, glycerol, formal, triglycerides such as Miglyol® products, optional water at concentrations up to 10%, as well as combinations of any of the foregoing excipients or other materials known to those of ordinary skill. Alternatively the compounds may be formulated in non-polar solvents such as vegetable and seed oils, for instance, cottonseed oil or peanut oil. For transmucosal administration, penetrants appropriate to the barrier to be permeated are used in the formulation. Such penetrants are generally known in the art.

In addition to the above-described formulations, concentrated compositions of compounds of the invention may be made, which may be diluted for use on site. Preparation of such concentrated compositions saves costs of shipping or storing large amounts of diluents, particularly water.

Administration

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, intramammary, aural or intraocular.

As discussed above, one method of administration of the compounds is by inclusion in the drinking water of the subject, since they are water-soluble.

Alternatively, one may administer the compound in a local rather than systemic manner, for example, by preparation as a salve or topically applied formulation that is applied directly to the infected area or by injection of the compound directly into infected tissue. In either case, a sustained release formulation may be used.

Thus, administration of the compounds of the invention, or their pharmaceutically acceptable solvates, in pure form or in an appropriate pharmaceutical composition can be carried out via any of the accepted modes of administration or agents for serving similar utilities. The routes of administration can be any known to those of ordinary skill. The inventive compounds are given to those in need thereof in any art recognized form, i.e. solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, adjuvants, etc.

Dosage

A therapeutically effective amount refers to an amount of compound effective to prevent and/or minimize microbial infection, and/or treat, alleviate and/or ameliorate symptoms due to a microbial infection. Determination of a therapeutically effective amount is well within the capability of those skilled in the art, especially in light of the disclosure herein.

For any compound used in the methods of the invention, the therapeutically effective amount can be estimated initially from known properties of the antibiotic agent that is released by the inventive prodrug compounds. Then, the dosage can be formulated for use in animal models so as to achieve a circulating concentration range that is at or greater than the minimum inhibitory concentration ("MIC") as previously known to the art. Such information can then be used to more accurately determine dosages useful in patients.

Therapeutic efficacy of the compounds described herein can be determined by standard pharmaceutical procedures in cell cultures or experimental animals. For example, the minimum inhibitory concentration ("MIC") is determined according to the guidelines laid down by the Clinical and Laboratory Standards Institute (CLSI)". Similarly, the toxicity of the compounds described herein can be depicted as $LD_{50}$ of the compound, which is a lethal dose for 50% of subjects in a group treated with a particular compound.

The data obtained can be used to formulate a range of dosages useful in patients. The dosage, of course, may vary depending upon the dosage form and route of administration. The exact formulation, route of administration and dosage can be selected by the individual clinician in view of the patient's condition. (See e.g. Fingl, et al., 1975, in "The Pharmacological Basis of Therapeutics", Ch. 1 p. 1). Broadly, the inventive compounds are administered to an animal in need of such treatment in a dose effective to reach and/or maintain concentrations of released antibiotic in plasma and body tissues at levels effective for the purpose, whether to treat and eliminate susceptible infectious microorganisms or to prevent new infection, for a sufficient time period to accomplish the desired goal. The skilled artisan will appreciate that the following estimated dose ranges are adjustable based on clinical response, as well as accounting for the relative amount of the phenicol antibiotic release from each respective prodrug compound. For example, for subcutaneous administration, the inventive compounds are generally administered at a dose ranging from about 1 mg to about 150 mg/kg of body weight. Frequency of administration can also range from a single dose per day to multiple doses per day. For oral administration, the dose will preferably be administered once per day.

Dosage amount and interval may be adjusted individually to provide plasma levels of the compound that are sufficient to maintain a concentration above or equal to the MIC or any other desired level. Such plasma levels are often referred to as minimum effective concentrations (MECs). The MEC will vary for each compound but can be estimated from in vitro data, e.g., the concentration necessary to achieve greater than 80% inhibition of a microbial population. The MEC may be ascertained using the assays described herein. Dosages necessary to achieve the MEC will depend on the individual characteristics of the compound and, or on the animal and/or route of administration. HPLC assays or bioassays can be used to determine plasma concentrations of the compound and/or its corresponding active product.

Dosage intervals can also be determined using MEC value. Compounds should be administered using a regimen that maintains plasma levels above the MEC for 10-90% of the time.

In cases of local administration or selective uptake, the effective local concentration of the drug may not be related to plasma concentration and other procedures known in the art may be employed to determine the correct dosage amount and interval.

The composition may be administered once daily or divided into multiple doses. Often only one dose will be sufficient to treat the infection. In some circumstances one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The amount of a composition administered will, of course, be dependent on the patient being treated, pathogen or bacteria causing the infection, the severity of the infection, the manner of administration, i.e., oral, intravenous, topical, etc., and the judgement of the prescribing physician, veterinarian, etc.

The inventive compound will generally be administered at a dose ranging from about 1 mg to about 150 mg/kg body weight in cattle, when using the subcutaneous route. Preferably, the dose ranges from about 20 mg to about 70 mg/kg body weight. More preferably the dose is about 60 mg/kg. However, when the inventive compound is administered via the intra-muscular (IM) route, the dose is preferably administered twice, with the administration of the second dose being about 24 to about 48 hours after the administration of the first dose.

In swine, the inventive compound will generally be administered in a dose ranging from about 10 mg to about 150 mg/kg body weight. Preferably the dose ranges from about 20 mg to 70 mg/kg body weight. In accordance with this invention, the prodrug is preferably administered to swine via their drinking water.

In poultry, the inventive compound will generally be administered in a dose ranging from about 10 mg to 150 mg/kg body weight. Orally, the prodrug will be administered in drinking water daily, for as long as is clinically indicated, e.g., for from about three to about seven days. In all the above cases, the prodrugs in drinking water can be administered either in a "bulk tank" or in a "proportioner". The final concentration will generally range from 50 mg/gallon to 700 ml/gallon. Preferably the concentration ranges from about 100 mg/gallon to about 600 mg/gallon. More preferably, the final concentration is about 500 mg/gallon. Such administration of prod rugs in drinking water may continue for a period ranging from 1 to 10 days. More preferably, it will continue for 5 consecutive days, or until the symptoms of respiratory disease are under control.

Administration to Aquatic Animals

An embodiment of the invention includes methods of eliminating, reducing or preventing bacterial infections in fish or aquatic invertebrates. The methods include administering an effective amount of a compound of the invention to an aquatic animal in need thereof. In most aspects of this embodiment, administering is achieved by either feeding the animal an effective amount of the inventive compound or by immersing the animal or animal population in a solution which contains an effective amount of the active compound in solution. It is to be further understood that the inventive compound can be administered by application of the drug to a pool or other water-holding area containing the animal, and allowing the animal to absorb the compound through their gills or otherwise allowing the dosage of the inventive compound to be taken in. For individual treatment of specific animals, such as a particular fish, e.g., in a veterinary or aquarium setting, direct injection or injection of osmotic release devices comprising the inventive compound, alone or in combination with other agents, is an optional method of administering the inventive compound.

The dose of the inventive compounds that is effective for reducing, eliminating, or preventing the bacterial infection in fish or other aquatic species can be routinely determined by a veterinarian using the parameters and methods discussed supra for other types of animals, although it may vary depending on the species of fish treated, the particular microorganisms involved, and the degree of infection. For aquaculture indications, the inventive compounds will generally be administered at a dosage of about 1 mg/kg to about 70 mg/kg, and preferably from 10 mg/kg to 30 mg/kg. Suitable routes of administering include: intravenously, subcutaneously, intramuscularly and/or by spraying or dipping the aquatic species as needed, and/or by directly adding the compound into the water in a holding volume.

For oral administration, the inventive compounds may be administered at the doses specified above from about 10 to about 15 days.

While the active ingredient can be administered separately from food it is contemplated that in a preferred aspect that the active will be incorporated into the fish feed. A medicated fish feed may be prepared by incorporating a suitable amount of compound of the present invention into a commercially available fish feed product to achieve the desired dosing levels. The amount of compound of the present invention incorporated into the fish feed will depend on the rate at which the fish are fed. For fish fed at the rate of about 0.2% to 4% of biomass/day, the medicated feed preferably contains from about 50 to 10,000 mg per kg of feed, and more preferably, from about 100 to 2,000 mg per kg of feed.

Although compounds of the present invention can be incorporated into a feed mixture prior to pelleting the medicated feed is preferably formed by coating feed pellets with compound of the present invention.

Any fish species, including fresh water and salt water varieties, as well as invertebrate aquatic species, an enumerated hereinabove can be treated with the compounds of the present invention to treat or prevent bacterial infections.

Combinations with Other Agents and Treatment Modalities

It is also contemplated to administer the inventive prodrug compounds in combination, simultaneously, or sequentially (e.g. in the same composition or in separate compositions) with other useful art-known medicinal agents. Such medicinal agents include, e.g., other microbiocides, e.g., antibiotics, antifungals, and antivirals, ecto- and endoparasiticides, and so forth, as well as nutritional supplements, feed additives and the like. For example, it is contemplated to administer any art-known standard (non-prodrug) phenicol such as florfenicol, chloramphenicol or thiamphenicol themselves in combination with the inventive compounds. Processes for the manufacture of these antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361, hereby incorporated by reference. Other analogs and/or prodrugs of chloramphenicol and thiamphenicol have been disclosed and such analogs also can be used in the compositions and methods of the present invention [see e.g., U.S. Pat. Nos. 7,041,670, and 7,153,842, both of which are hereby incorporated by reference in their entireties]. When the antibiotic compound is florfenicol, the concentration of florfenicol typically is from about 10% to about 50%, with the preferred level between about 20% and about 40%, even more preferred being at least about 30% (in these cases, given as w/w in the case of solid compositions and w/v in the case of liquid compositions).

Another useful antibiotic compound for use in a combination with the inventive compounds is tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695, hereby incorporated by reference. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly *Pasteurella haemolytica* infections in cattle when administered by injection over a 4 day treatment period. Accordingly, tilmicosin may be used in treatment of, for example, neonatal calf pneumonia and bovine respiratory disease. When tilmicosin is present, it is present in an amount of about 1% to about 50% w/v, preferably 10% to about 50%, and in a particular embodiment, 30%.

Another useful antibiotic for use in combination with the inventive compounds is tulathromycin. Tulathromycin may be prepared in accordance with the procedures set forth in U.S. Pat. No. 6,825,327, which is hereby incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight (w/v).

Another useful antibiotic for use in combination with the inventive compounds is the fluoroquinolones family of antibiotics, such as, for example, enrofloxacin, danofloxacin, difloxacin, orbifloxacin and marbofloxacin. In the case of enrofloxacin, it may be administered in a concentration of about 100 mg ml. danofloxacin may be present in a concentration of about 180 mg/ml.

Other useful macrolide antibiotics for use in combination with the inventive compounds include compounds from the class of ketolides, or, more specifically, the azalides. Such compounds are described in, for example, U.S. Pat. Nos. 6,514,945, 6,472,371, 6,270,768, 6,437,151 and 6,271,255, 6,239,112, 5,958,888, and 6,339,063 and 6,054,434, all of which are hereby incorporated by reference in their entireties.

Other useful antibiotics for use in combination with the inventive compounds include the tetracyclines, particularly chlortetracycline and oxytetracycline.

Other antibiotics may include beta-lactams such as one of the penicillins, e.g., penicillin G, penicillin K, ampicillin, amoxicillin, or a combination of amoxicillin with clavulanic acid or other beta-lactamase inhibitors. Additional particular beta-lactams include the cephalosporins such as, for example, ceftiofur, cefquinome, etc.

Additionally, the present invention optionally includes a composition for the treatment of a microbial and parasitic infection in an animal that comprises one or more of the above-listed antibiotics admixed and/or in combination with one or more of the inventive compounds, and an optional carrier and/or excipient.

For all of the methods and the inventive compounds described herein, it is also contemplated that the identified compounds are readily employed in combination with one or more art-known agents for killing or controlling various types of parasites, e.g., including all of the ecto- and endoparasites described herein. Thus, although the inventive compounds and methods are preferred over previously known agents and methods of using previously known agents, in certain optional embodiments they are contemplated to be employed in combination, simultaneously, or sequentially (e.g. in the same composition or in separate compositions), with other art-known agents or combinations of such art-known agents employed for killing or controlling various types of pests.

These additional agents for use in combination with the inventive compounds include, for example, art-known anthelmintics, such as, for example, avermectins (e.g. ivermectin, moxidectin, milbemycin), benzimidazoles (e.g. albendazole, triclabendazole), salicylanilides (e.g. closantel, oxyclozanide), substituted phenols (e.g. nitroxynil), pyrimidines (e.g. pyrantel), imidazothiazoles (e.g. levamisole) and praziquantel.

Additional art-known agents for killing or controlling pests for use in combination with the inventive compounds include the organophosphate pesticides. This class of pesticides has very broad activity, e.g. as insecticides and, in certain instances anthelmintic activity. Organophosphate pesticides include, e.g., dicrotophos, terbufos, dimethoate, diazinon, disulfoton, trichlorfon, azinphos-methyl, chlorpyrifos, malathion, oxydemeton methyl, methamidophos, acephate, ethyl parathion, methyl parathion, mevinphos, phorate, carbofenthion, phosalone, to name but a few such compounds. It is also contemplated to include combinations of the inventive methods and compounds with carbamate type pesticides, including, e.g., carbaryl, carbofuran, aldicarb, molinate, methomyl, etc., as well as combinations with the organochlorine type pesticides. It is further contemplated to include combinations with biological pesticides, including e.g. repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *Bacillus thuringiensis*, chlorobenzilate, formamidines, (e.g. amitaz), copper compounds, e.g., copper hydroxide, cupric oxychloride sulfate, cyclotron, cypermethrin, dicofol, endosulfan, esenfenvalerate, fenvalerate, lambda-cyhalothrin, methoxychlor and sulfur.

In addition, for all of the methods and new compounds described herein, it is further contemplated that the identified compounds can be readily employed in combination with synergists such as piperonyl butoxide (PBO) and triphenyl phosphate (TPP); and/or with Insect Growth Regulators (IGRs) and Juvenile Hormone Analogues (JHAs) such as diflubenzuron, cyromazine, methoprene, etc., thereby providing both initial and sustained control of parasites (at all stages of insect development, including eggs) on the animal subject, as well as within the environment of the animal subject.

Combinations with cyclodienes, ryania, KT-199 and/or older art-known anthelmintic agents, such as avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), praziquantel and some organophosphates such as naphthalophos and pyraclofos, are also contemplated to be employed in such combinations.

In particular, additional antiparasitic compounds useful within the scope of the present invention are preferably comprised of the class of avermectin compounds. As stated above, the avermectin family of compounds is a series of very potent antiparasitic agents known to be useful against a broad spectrum of endoparasites and ectoparasites in mammals.

A preferred compound for use in combination with the inventive compounds within the scope of the present invention is ivermectin. Ivermectin is a semi-synthetic derivative of avermectin and is generally produced as a mixture of at least 80% 22,23-dihydroavermectin $B1_a$ and less than 20% 22,23-dihydroavermectin $B1_b$. Ivermectin is disclosed in U.S. Pat. No. 4,199,569, hereby incorporated by reference. Ivermectin has been used as an antiparasitic agent to treat various animal parasites and parasitic diseases since the mid-1980s.

Abamectin is an avermectin that is disclosed as avermectin B1a/B1 b in U.S. Pat. No. 4,310,519, which is hereby incorporated by reference in its entirety. Abamectin contains at least 80% of avermectin $B1_a$ and not more than 20% of avermectin $B1_b$.

Another preferred avermectin is doramectin also known as 25-cyclohexyl-avermectin $B_1$. The structure and preparation of doramectin, is disclosed in U.S. Pat. No. 5,089,480, which is hereby incorporated by reference in its entirety.

Another preferred avermectin is moxidectin. Moxidectin, also known as LL-F28249 alpha is known from U.S. Pat. No. 4,916,154, which is hereby incorporated by reference in its entirety.

Another preferred avermectin is selamectin. Selamectin is 25-cyclohexyl-25-de(1-methylpropyl)-5-deoxy-22,23-dihydro-5-(hydroxyimino)-avermectin B1 monosaccharide.

Milbemycin, or B41, is a substance which is isolated from the fermentation broth of a milbemycin producing strain of *Streptomyces*. The microorganism, the fermentation conditions and the isolation procedures are more fully described in U.S. Pat. Nos. 3,950,360 and 3,984,564.

Emamectin (4"-deoxy-4"-epi-methylaminoavermectin B1), which can be prepared as described in U.S. Pat. Nos. 5,288,710 or 5,399,717, is a mixture of two homologues, 4"-deoxy-4"-epi-methylaminoavermectin B1a and 4"-deoxy-4"-epi-methylaminoavermectin B1b. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is emamectin benzoate.

Eprinomectin is chemically known as 4"-epi-Acetylamino-4"-deoxy-avermectin B1. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The compositions of the present invention optionally comprise combinations of one or more of the following antiparasite compounds (parasiticides):

The antiparasite imidazol [1,2-b]pyridazine compounds as described by U.S. Patent Application Publication No. 2005/0182059, incorporated by reference herein.

The antiparasite 1-(4-mono and di-halomethylsulphonylphenyl)-2-acylamino-3-fluoropropanol compounds, as described by U.S. Patent Application Publication No. 2005/00182139, incorporated by reference herein.

The antiparasite trifluoromethanesulfonanilide oxime ether derivative compounds, as described by U.S. Patent Application Publication No. 2006/0063841, incorporated by reference herein.

The antiparasite phenyl-3-(1H-pyrrol-2-yl)acrylonitrile compounds, as described by U.S. Patent Application Publication No. 2006/0128779, incorporated by reference herein.

The antiparasite N-[(phenyloxy)phenyl]-1,1,1-trifluoromethanesulfonamide and N-[(phenylsulfanyl)phenyl]-1,1,1-trifluoromethanesulfonamide derivatives, as described by U.S. Patent Application Publication No. 2006/0283695, incorporated by reference herein.

The antiparasite N-phenyl-1,1,1-trifluoromethanesulfonamide hydrazone compounds, as described by U.S. Patent Application Publication No. 2007/0238700, incorporated by reference herein.

The compositions of the present invention may also be employed in combination with a flukicide. Suitable flukicides include, for example, triclabendazole, fenbendazole, albendazole, clorsulon and oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g. in a combined composition and/or in separate dosage forms. Art-known antibiotics suitable for this purpose include, for example, those listed hereinabove.

Further, it is also contemplated that the inventive methods and compounds be advantageously employed in combination, simultaneously or sequentially, with art-known animal health remedies e.g., trace elements, vitamins, anti-inflammatories, anti-infectives and the like, in the same or different compositions.

Suitable anti-inflammatory agents include, e.g., both steroidal and non-steroidal anti-inflammatory agents. Non-steroidal anti-inflammatory agents, including their racemic mixtures or individual enantiomers where applicable, can include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

In a particular embodiment, a compound of the present invention is employed in combination with flunixin, [see, e.g., U.S. Pat. No. 6,790,867 B2, which is hereby incorporated by reference in its entirety.] In a related embodiment, the present invention provides a pharmaceutical composition comprising a compound of the present invention and flunixin.

Steroidal anti-inflammatory agents include, for example, glucocorticoid agents such as dexamethasone, cortisone, hydrocortisone, prednisone, beclomethasone, betamethasone, flunisolide, methyl prednisone, para methasone, prenisolone, triamcinolome, alclometasone, amcinonide, clobetasol, fludrocortisone, difluorosone diacetate, fluocinolone acetonide, fluoromethalone, flurandrenolide, halcinonide, medrysone, mometasone, and pharmaceutically acceptable salts and mixtures thereof.

reagents. These reagents can be prepared by generally known methods described in the literature (e.g. "March's Advanced Organic Chemistry: Reactions, Mechanisms, and Structure", 5th Edition Michael B. Smith, Jerry March, Jan. 15, 2001; Wiley-Interscience).

One strategy for preparation of these carbonates and esters bearing a terminal nitrogen based positively charged nitrogen functionality employs the use of an appropriately protected amino functionality as shown in the Scheme 1 below (a large selection of protecting groups PG for amino group protection and methods for using them is described in "Protective Groups in Organic Synthesis", Theodora W. Greene, Peter G. M. Wuts; May 15, 1999 Wiley-Interscience)

Scheme 1

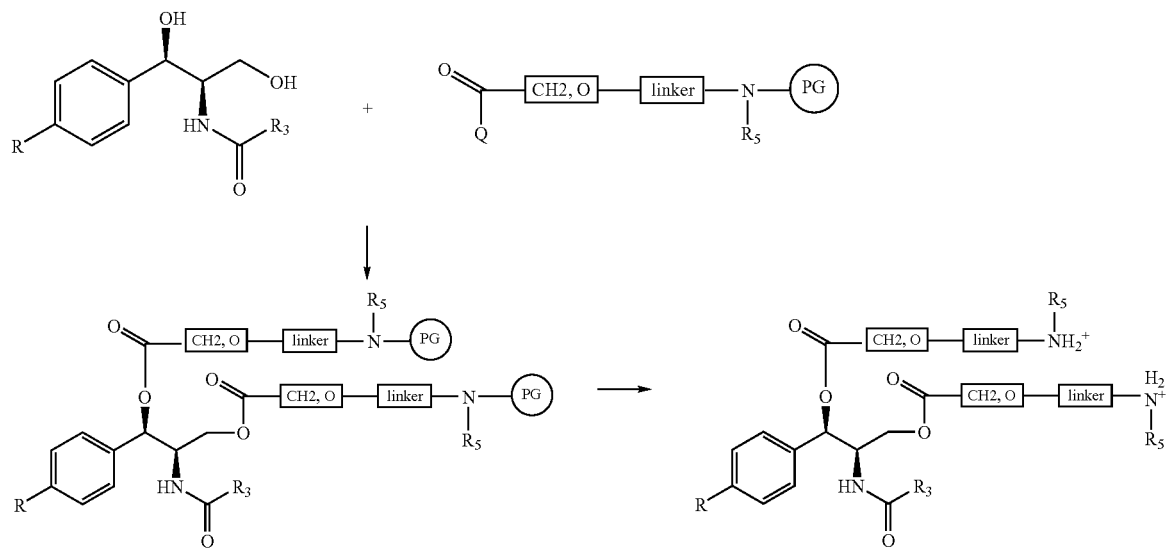

Packaging

The compositions may, if desired, be presented in a pack, sachet or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Flood and Drug Administration for prescription drugs or of an approved product insert. Compositions comprising a compound of the invention formulated in a compatible pharmaceutical carrier may also be prepared, placed in an appropriate container, and labeled for treatment of an indicated condition. In an optional embodiment, the packaging comprises glass or plastic vials or other containers comprising multiple doses.

The following is a general description of a process that may be used to prepare compounds of the present invention:

Carbonates and esters of chloramphenicol, thiamphenicol or an analog of either bearing a terminal nitrogen based positively charged nitrogen functionality can be conveniently prepared by reaction of the phenicol in question with appropriately activated carboxylic acids or alkoxycarbonic acid Chloramphenicol, thiamphenicol, or an analog of either, is reacted with the activated carboxylic acid reagent (e.g., acyl chloride, acyl imidazolide, carboxylic acid hydroxysuccinimide ester, carboxylic acid perfluorophenol ester, carboxylic acid carbondiimide adduct and like) or activated alkoxy carbonic acid reagent (chloroformate or an alternative carbonating reagent having leaving group other than chloride—vide supra) with the nucleophilic displacement of group Q (when $R_3$=$CH_2NH_2$ a protection of the amino group is necessary before functionalization of hydroxy groups). Most common reagents of this type utilize Q=chlorine. The reaction may be facilitated by the addition of a catalyst like a trialkylamine, pyridine, a 4-alkylpyridine, a 4-diaminoalkylpyridine or a combination thereof. Alternatively the carboxylic acid can be activated in situ by addition of the appropriate activating reagent to the reaction mixture containing the phenicol in question and the carboxylic acid. Formation of the initial ester or carbonate intermediate can be conveniently performed in variety of solvents. Suitable solvents include for example, chlorinated solvents such as dichloromethane and 1,2-dichloroethane; ester solvents such as ethyl acetate, isopropyl acetate, isoamyl acetate, ethylene glycol diacetate, propylene glycol diacetate, glycerol triacetate; monoether solvents such as diethyl ether, diisopropyl ether, methyl tert-butyl ether; polyether solvents such as ethylene glycol ethers, dimethyl ethylene glycol ether, diethylene glycol ethers: diethylenelycol dimethyl ether, diethylene glycol diethyl ether; formaldehyde acetal ethers such as dimethoxymethane, diethoxymethane, dibutoxymethane; cyclic ethers such as tetrahydrofuran, 1,3-dioxolane, 1,4-dioxane; ketone solvents such as acetone methyl ethyl ketone, methyl isobutyl ketone; mixed ether/ester solvents as represented by monoethers of ethylene and diethylene glycol such as 2-methoxyethyl acetate, 2-ethoxyethyl acetate, 2-(methoxy-ethoxy)ethyl acetate, 2-(ethoxy-ethoxy)ethyl acetate. The examples provided below exemplify the use of tetrahydrofuran as the solvent.

Typically the reaction is conducted by adding 2.5-3.0 equivalents of corresponding chloroformate or other reactive alkoxycarbonic acid derivative in tetrahydrofuran solution to the tetrahydrofuran solution containing a phenicol, 2.0 equivalents of triethylamine and 1.0 equivalent of 4-N,N-dimethylaminopyridine at 0° C. and allowing the reaction to proceed to completion.

After formation of the terminal amine protected ester or carbonate of chloramphenicol, thiamphenicol or an analog of either, the deprotection of the amine functionality is performed by a standard deprotection method depending on the character of the protecting group. For acid-sensitive protecting groups the deprotection can lead directly to the desired salt form (e.g. hydrochloride when the appropriate acid is used for deprotection. When the deprotection method produces the free amine the desired salt form can be prepared by adding the acid to the reaction mixture or by performing conversion of the amine to the appropriate salt in a separate step.

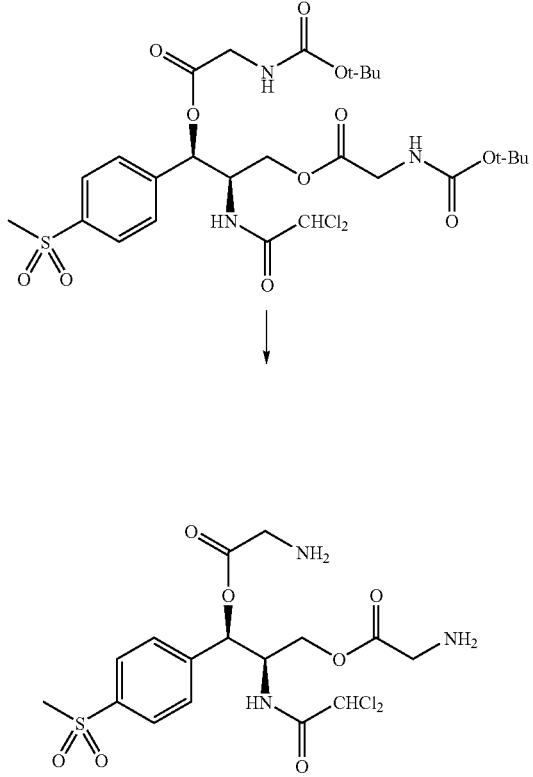

An alternative strategy for preparation of carbonates and ester prodrugs bearing a terminal nitrogen-based positively charged functionality may involve a nitrogen-containing "masked amine" functionality which is in a later stage converted into desired amine. Examples of typical nitrogen-containing functionalities for this purpose (and respective methods from conversions into amine) are: nitro (reduction), azido (reduction), nitrile (reduction to $CH_2NH_2$) and primary amide (Curtius rearrangement).

Scheme 2

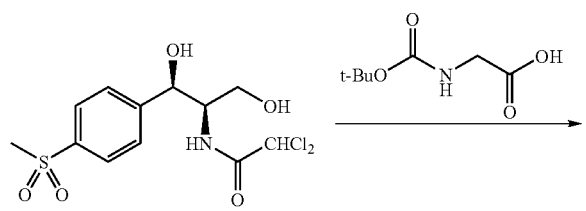

Scheme 3

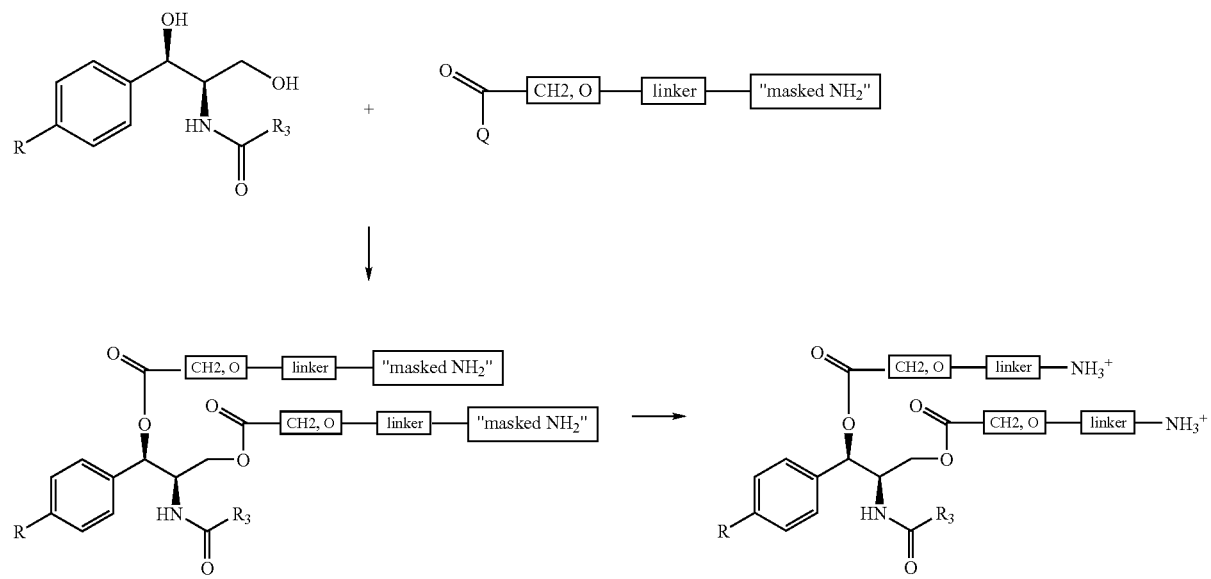

The following example shows preparation of a specific compound of the present invention using thiamphenicol as the starting material for preparations of corresponding thiamphenicol prodrugs. Analogous preparations can be applied to chloramphenicol and its analogs and to thiamphenicol analogs provided that the reaction schemes are designed with regard to the compatibility of functional group interconversions.

Another convenient strategy for preparation of the prodrugs of the present invention involves displacement of the leaving group LG on the carbonate or ester moiety attached to the phenicol compound. This approach can be particularly convenient for prodrug moieties bearing a quaternary ammonium nitrogen but it can be also used for the introduction off other amino functionalities.

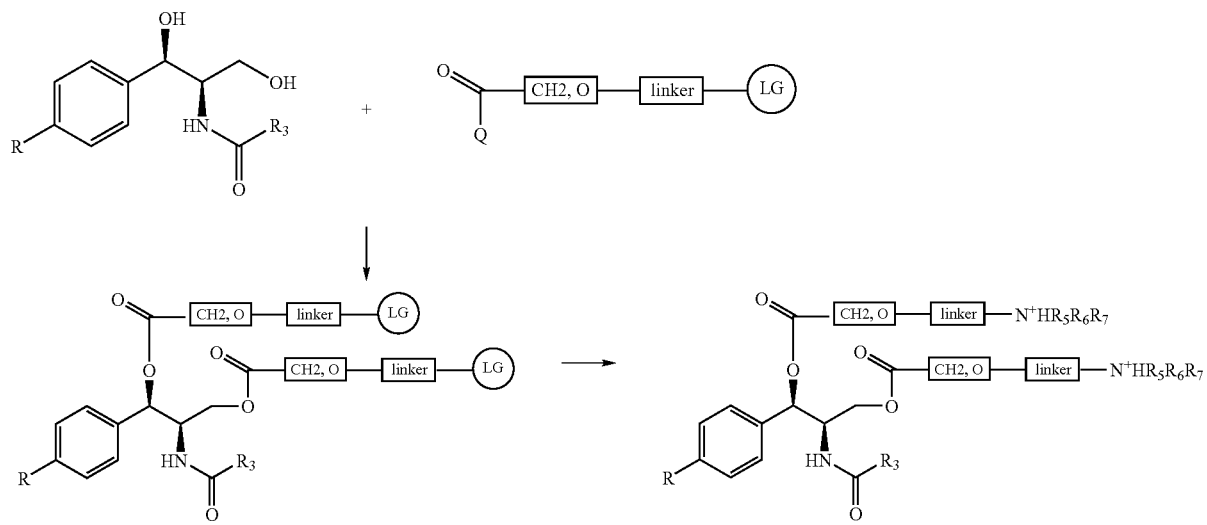

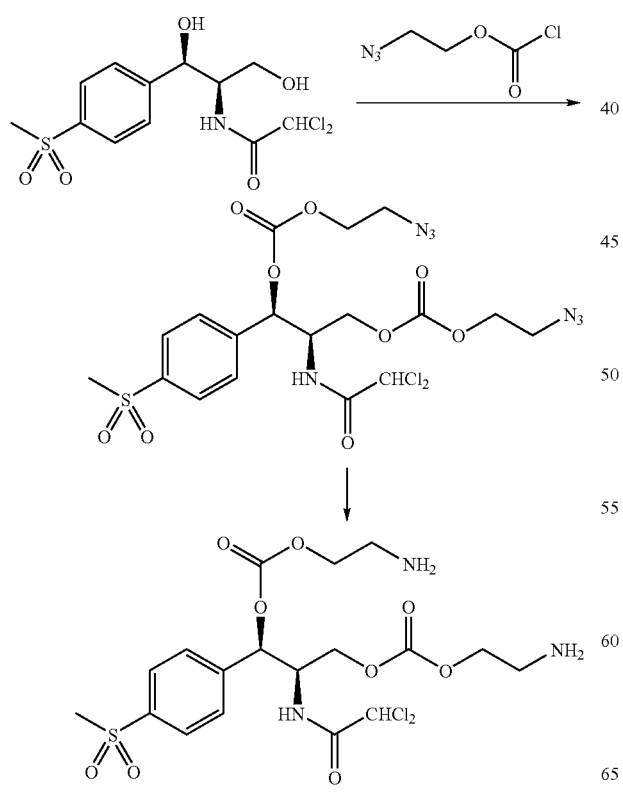

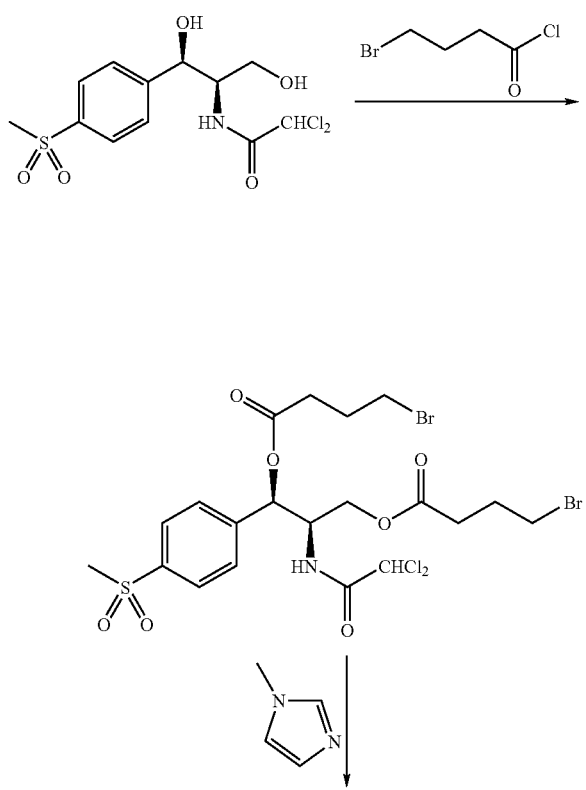

-continued

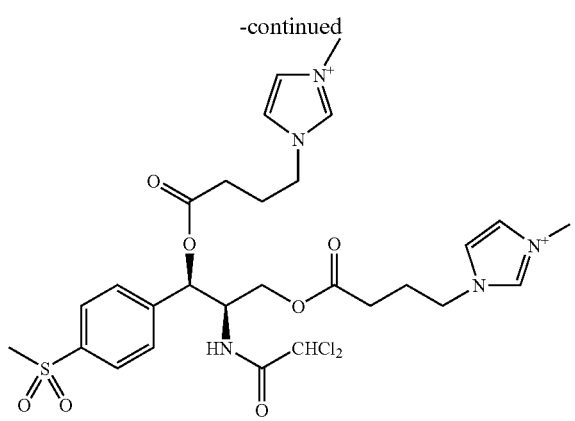

A convenient method for preparation of the amino acid ester prodrug of thiamphenicol may utilize a combination of methods from Schemes 3 and 5 as shown below for the preparation of a thiamphenicol prodrug:

For the preparation of ester prodrugs which contain an alpha-amino acid that is not directly attached to the phenicol in question at least two general strategies can be employed. In one strategy the distal amino acid is incorporated into the prodrug moiety before attaching it to the phenicol while in the other one the attachment of the distal amino acid can be performed after attaching the first fragment of the prodrug moiety to the phenicol.

The two strategies which can be conveniently used for preparation of such prodrugs are exemplified in Scheme 8.

Scheme 7

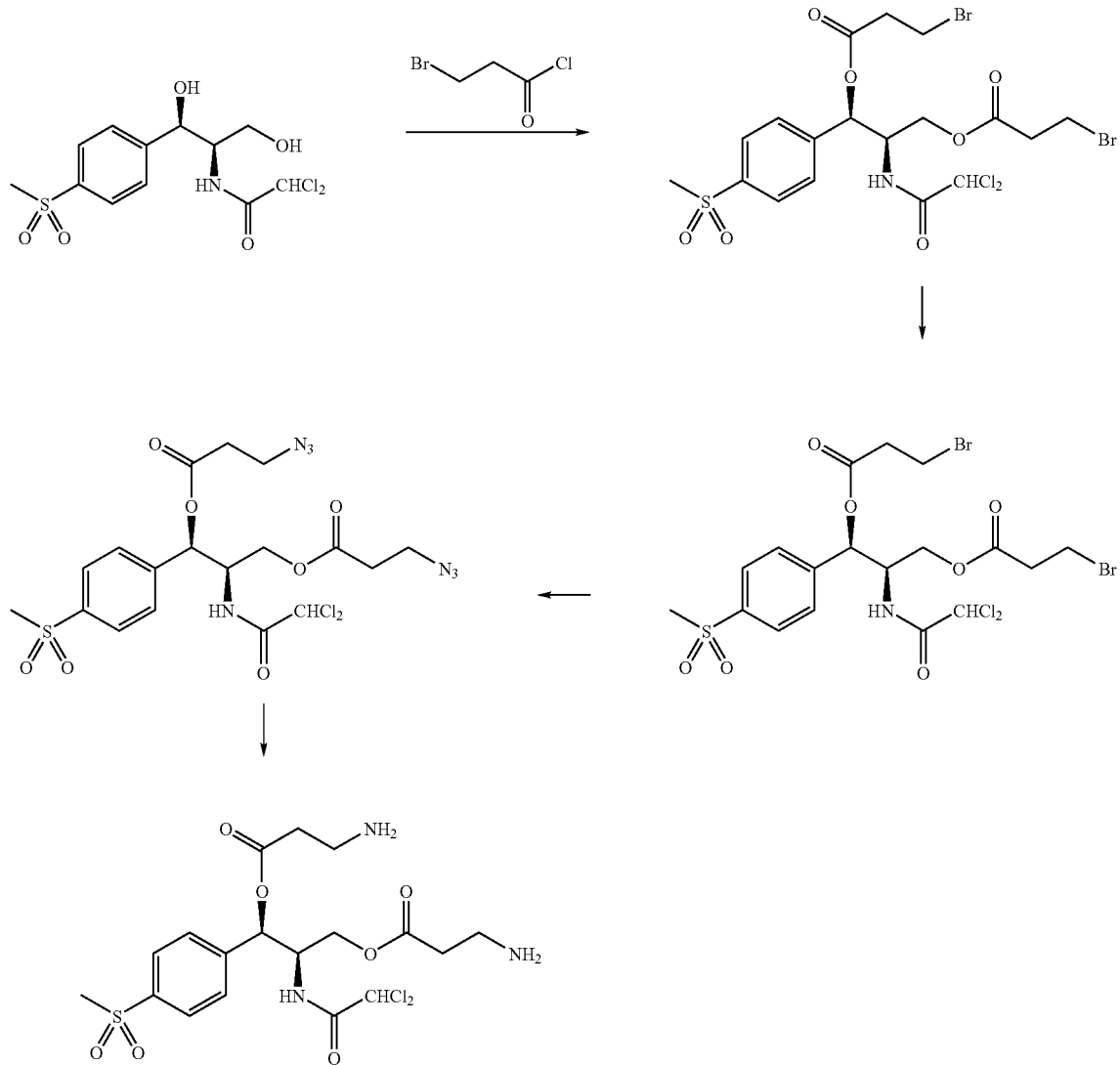

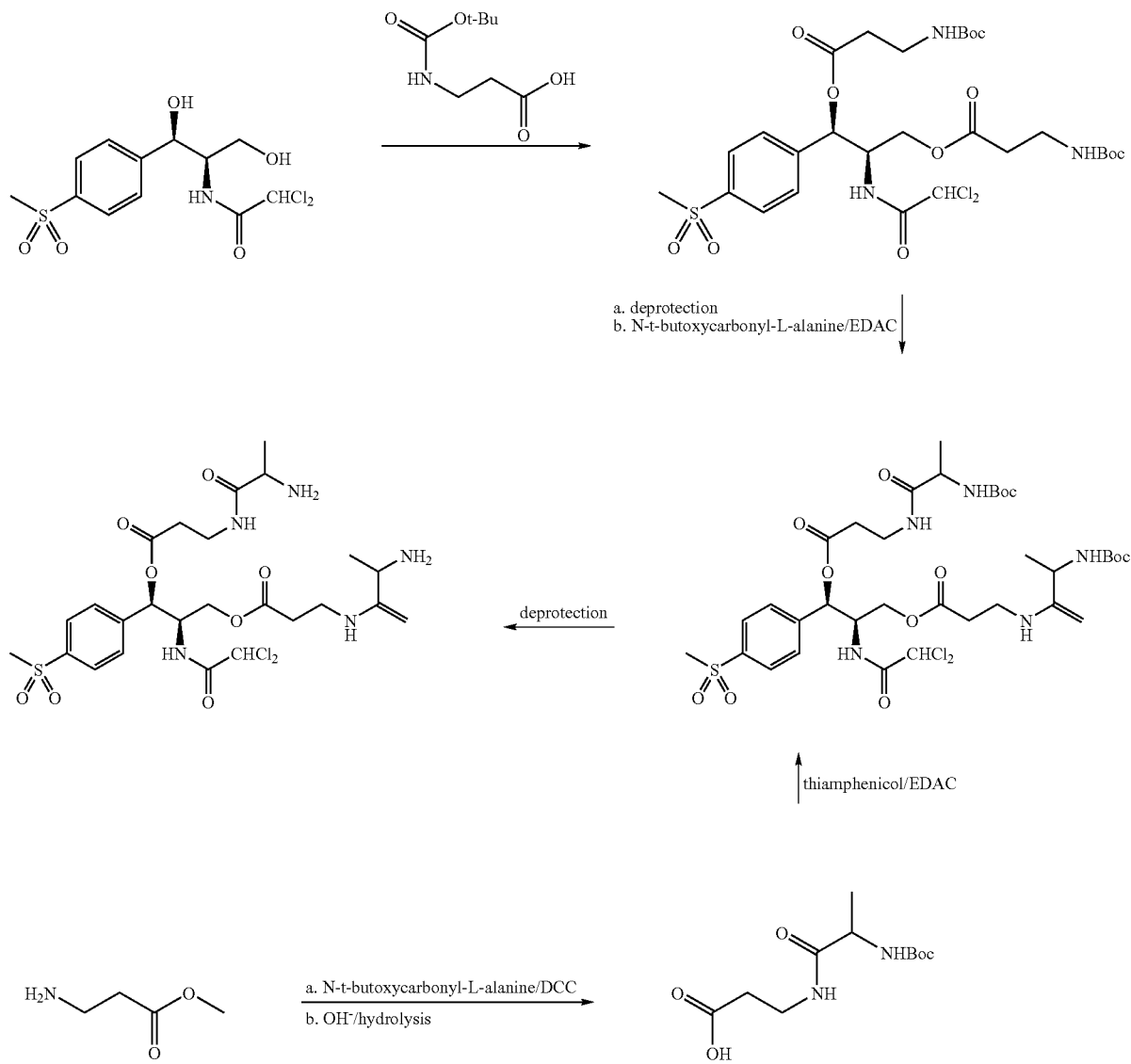
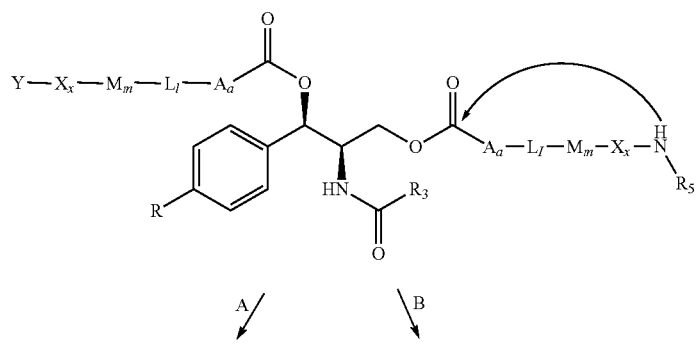
Stability of Prodrugs and Parent Phenicol Release

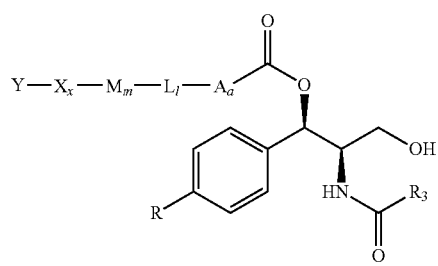
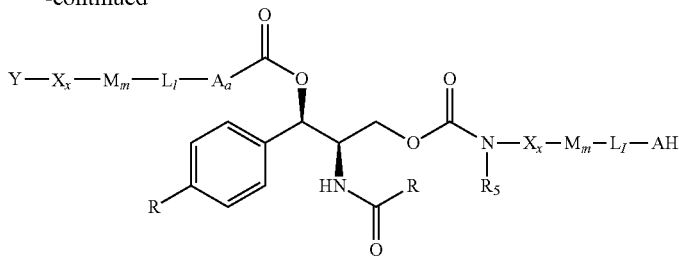

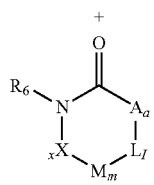

A non-enzymatic release of chloramphenicol or thiamphenicol or an analog of either can take place when there is a possibility of intramolecular displacement of the phenicol in question by the terminal amine functionality (Scheme 9, route A). The rates of such processes depend greatly on the substrate and the pH of the solution. For this displacement to occur the terminal amine needs to be primary or secondary and the pH needs to be sufficiently high to allow for the unprotonated amine to exist in unprotonated form in meaningful concentration. Additionally the sum of x+m+l+a needs to be 3 or 4 to allow easy formation of the 5 or 6-membered ring upon cyclization. Substitution of the terminal amine also can affect the rate of such cyclization mediated release of the phenicol dramatically. Acylation of the amine entirely prevents such cyclization white alkyl substitution can slow the cyclization considerably relative to the unsubstituted primary amine. The ability to undergo cyclization and release the phenicol in question can largely determine the stability of prodrugs when the pH of the aqueous solution is adjusted from original acidic pH for aqueous solutions of crude hydrochlorides of a prodrug to close to the physiological pH of 7.4. Prodrug moieties at secondary alcohol group can be subject to analogous cyclization mediated release of the parent phenicol.

A phenicol release induced by a change of pH when the prodrug solution that has been given orally reaches the intestine is entirely acceptable from the standpoint of the oral bioavailability of the phenicol. Depending on the rate of release of the phenicol after intestinal pH adjustment of the ingested prodrug solution, the release and absorption of free phenicol may be responsible for varying degrees of bioavailability of it from different soluble prodrugs. For more stable prodrugs a major component of the oral bioavailability of the phenicol may be due to the oral absorption of intact prodrug followed by fast systemic release by an enzymatically mediated process.

A competing process induced by the change of the pH of the prodrug solution, which is only possible for carbonate prodrugs (A=oxygen, Scheme 9, route B), also occurs by the initial nucleophilic attack of the terminal primary secondary amine on the carbonyl functionality linking the prodrug moiety to the phenicol residue. Prodrug moieties at secondary alcohol group can also be subject to analogous undesired rearrangement of the prodrug.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the an in light of the teachings of this invention that certain changes and modifications may be made thereto without departing from the spirit or scope of the appended claims.

What is claimed is:

1. A compound having the Formula (I)

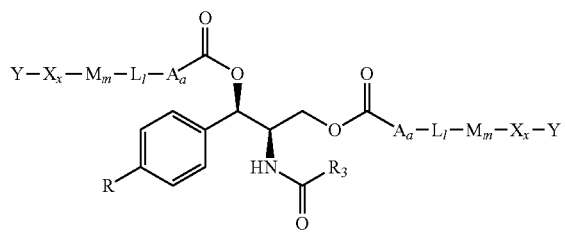

in which:

R is selected from the group consisting of

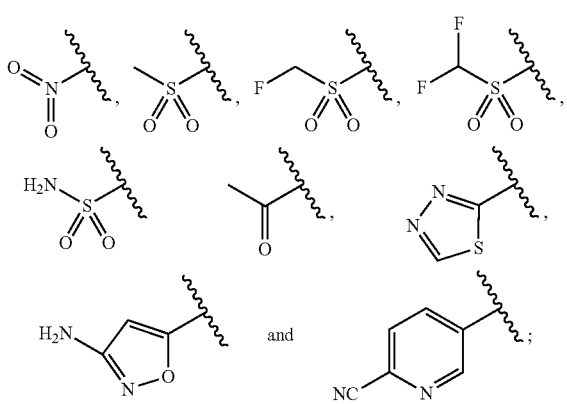

$R_3$ is selected from the group consisting of dichloromethyl, difluoromethyl, chlorofluoromethyl, chloromethyl, methyl, cyanomethyl, azidomethyl, and aminomethyl; and —O—C(=O)-$A_a$-$L_l$-$M_m$-$X_x$—Y is selected from the group consisting of:

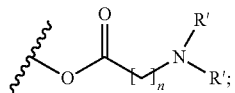

wherein n is an integer from 2-6 and R' is H, Me or Et; and

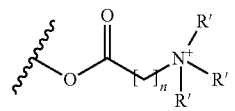

wherein n is an integer from 1 to 6 and R' is Me or Et; and pharmaceutically acceptable salts thereof.

2. A pharmaceutical composition comprising a therapeutically effective amount of a compound or salt according to claim 1 and a pharmaceutically acceptable diluent or carrier.

3. A composition according to claim 2 further comprising an effective amount of one or more additional medicinal agents.

4. A composition according to claim 3 in which the one or more additional medicinal agents are selected from microbiocides, anthelmintics, ecto- and endoparasticides, anti-fluke agents, anti-inflammatories, anti-infectives, hormones, dermatological preparations, including antiseptics and disinfectants, and immunobiologicals including vaccines and antisera.

5. A method of treating a microbial infectious disease or disorder in a subject comprising administering to said subject a therapeutically effective amount of a compound according to claim 1.

6. A method of treating a microbial infectious disease or disorder in a subject comprising administering to said subject a therapeutically effective amount of a composition according to claim 2.

* * * * *